US011998346B2

(12) United States Patent
Lee et al.

(10) Patent No.: US 11,998,346 B2
(45) Date of Patent: Jun. 4, 2024

(54) ELECTRONIC DEVICE AND METHOD FOR DETERMINING SLEEP-RELATED INFORMATION

(71) Applicant: SAMSUNG ELECTRONICS CO., LTD., Suwon-si (KR)

(72) Inventors: Wonkyu Lee, Suwon-si (KR); Hwan Shim, Suwon-si (KR); Hyunsu Kim, Yongin-si (KR); Seounghun Kim, Suwon-si (KR); Taeho Kim, Cheongju-si (KR); Sun-Kee Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1234 days.

(21) Appl. No.: 16/614,472

(22) PCT Filed: Apr. 13, 2018

(86) PCT No.: PCT/KR2018/004334
§ 371 (c)(1),
(2) Date: Nov. 18, 2019

(87) PCT Pub. No.: WO2018/212462
PCT Pub. Date: Nov. 22, 2018

(65) Prior Publication Data
US 2020/0205726 A1 Jul. 2, 2020

(30) Foreign Application Priority Data
May 19, 2017 (KR) .................. 10-2017-0062036

(51) Int. Cl.
*A61B 5/00* (2006.01)
*A61B 5/0205* (2006.01)
(Continued)

(52) U.S. Cl.
CPC .......... *A61B 5/4809* (2013.01); *A61B 5/0082* (2013.01); *A61B 5/0205* (2013.01);
(Continued)

(58) Field of Classification Search
CPC ... A61B 5/4815; A61B 5/4812; A61B 5/0816; A61B 5/024; A61B 5/0205;
(Continued)

(56) References Cited

U.S. PATENT DOCUMENTS

2009/0112069 A1\* 4/2009 Kanamori .............. A61B 5/113
600/300
2009/0134819 A1 5/2009 Noguchi et al.
(Continued)

FOREIGN PATENT DOCUMENTS

JP 2010-227469 10/2010
JP 5788293 9/2015
(Continued)

OTHER PUBLICATIONS

Office Action dated Jun. 29, 2021 in counterpart Korean Patent Application No. 10-2017-0062036 and English-language translation.
(Continued)

*Primary Examiner* — Olumide Ajibade Akonai
(74) *Attorney, Agent, or Firm* — Nixon & Vanderhye, P.C.

(57) ABSTRACT

An electronic device according to various embodiments comprises: a bio-signal detection sensor configured to acquire first and second biometric information on an object outside the electronic device; and a processor, wherein the processor can be configured to: acquire the first and second biometric information by using the bio-signal detection sensor; configure a first variance, in which the first biometric information is changed, and a second variance, in which the
(Continued)

second biometric information is changed; determining a state of the object related to the sleep on the basis of at least a part of the first variance and the second variance; and estimate a sleep latency related to the object on the basis of at least a part of the state.

19 Claims, 25 Drawing Sheets

(51) Int. Cl.
| | | |
|---|---|---|
| *A61B 5/024* | (2006.01) | |
| *A61B 5/0507* | (2021.01) | |
| *A61B 5/08* | (2006.01) | |
| *A61B 5/11* | (2006.01) | |
| *A61B 5/113* | (2006.01) | |
| *A61M 21/00* | (2006.01) | |
| *A61M 21/02* | (2006.01) | |
| *G01S 13/50* | (2006.01) | |
| *G01S 13/88* | (2006.01) | |
| *H05B 47/105* | (2020.01) | |

(52) U.S. Cl.
CPC .......... *A61B 5/0507* (2013.01); *A61B 5/1126* (2013.01); *A61B 5/113* (2013.01); *A61M 21/02* (2013.01); *G01S 13/50* (2013.01); *G01S 13/88* (2013.01); *H05B 47/105* (2020.01); *A61B 5/0022* (2013.01); *A61B 5/02444* (2013.01); *A61B 5/0816* (2013.01); *A61B 2560/0242* (2013.01); *A61M 2021/0027* (2013.01); *A61M 2021/0044* (2013.01)

(58) Field of Classification Search
CPC . A61B 5/4809; A61B 5/02055; A61B 5/1118; A61B 5/486; A61B 2560/0242; A61B 5/11; A61B 5/02405; A61B 5/681; A61B 5/4806; A61B 5/021; A61B 5/02438; A61B 5/0082; A61B 5/0507; A61B 5/1126; A61B 5/113; A61B 5/0022; A61B 5/02444; A61B 5/6887; A61B 5/7235; G01S 13/56; G01S 13/50; G01S 13/88; G01S 7/03; A61M 2230/42; A61M 21/02; A61M 2021/0027; A61M 2021/0044; G06F 16/636; G06V 40/70; G06V 40/15; H05B 47/105

See application file for complete search history.

(56) References Cited

U.S. PATENT DOCUMENTS

| | | | |
|---|---|---|---|
| 2014/0276245 A1 | 9/2014 | Tsutsumi et al. | |
| 2015/0164409 A1* | 6/2015 | Benson | A61B 5/1116 600/595 |
| 2016/0029966 A1* | 2/2016 | Salas-Boni | A61B 5/02055 600/347 |
| 2016/0151603 A1 | 6/2016 | Shouldice et al. | |
| 2016/0302677 A1* | 10/2016 | He | A61B 5/1102 |
| 2017/0055899 A1* | 3/2017 | Bandyopadhyay | A61B 5/743 |
| 2017/0094046 A1* | 3/2017 | Raymann | G08B 21/06 |
| 2017/0136348 A1* | 5/2017 | Hattori | A61B 5/7271 |
| 2017/0182284 A1* | 6/2017 | Ueya | A61M 21/02 |
| 2018/0078197 A1* | 3/2018 | Ware | G16H 40/63 |
| 2018/0078732 A1* | 3/2018 | Keshavan | A61M 21/02 |
| 2018/0325450 A1* | 11/2018 | Huang | A61B 5/4812 |

FOREIGN PATENT DOCUMENTS

| | | |
|---|---|---|
| KR | 10-2007-0039331 | 4/2007 |
| KR | 10-2007-0120827 | 12/2007 |
| WO | 2016/108751 | 7/2016 |

OTHER PUBLICATIONS

International Search Report for PCT/KR2018/004334 dated Aug. 23, 2018, 4 pages.
Written Opinion of the ISA for PCT/KR2018/004334 dated Aug. 23, 2018, 4 pages.
Notice of Patent Grant dated Nov. 29, 2021 in counterpart Korean Patent Application No. 10-2017-0062036 and English-language translation.

* cited by examiner

ELECTRONIC DEVICE AND METHOD FOR DETERMINING SLEEP-RELATED INFORMATION

This application is the U.S. national phase of International Application No. PCT/KR2018/004334 filed Apr. 13, 2018 which designated the U.S. and claims priority to KR Patent Application No. 10-2017-0062036 filed May 19, 2017, the entire contents of each of which are hereby incorporated by reference.

TECHNICAL FIELD

The disclosure relates to an electronic device for determining sleep-related information and a method of the same.

BACKGROUND ART

Sleep recovers the brain or the body having accumulation of fatigue through a sophisticated active interaction of the central nervous system. As described above, sleep is a factor influencing human health, and thus an electronic device for monitoring a sleep state of a user has been developed.

DISCLOSURE OF INVENTION

Technical Problem

An electronic device may need user engagement or intervention in order to measure sleep information of the user. In general, the user sleeps to take a rest and thus such user engagement or intervention may be inconvenient for the user sleeping.

Meanwhile, sleep latency from a time point at which the user intends to sleep to a time point at which the user falls asleep may be an important parameter to indicate a sleep state of the user. Accordingly, an electronic device for determining sleep latency without any user engagement or intervention may be required.

Various embodiments may provide an electronic device and a method for determining speed latency through a Radio Frequency (RF) sensor separated from the user.

The technical subjects pursued in the disclosure may not be limited to the above mentioned technical subjects, and other technical subjects which are not mentioned may be clearly understood, through the following descriptions, by those skilled in the art of the disclosure.

Solution to Problem

In accordance with an aspect of the disclosure, an electronic device is provided. The electronic device includes: a biometric signal detection sensor configured to acquire first biometric information and second biometric information on an object outside the electronic device; and a processor, wherein the processor is configured to acquire the first biometric information and the second biometric information through the biometric signal detection sensor, identify a first change of the first biometric information and a second change of the second biometric information, determine a state of the object related to sleep on the basis of at least a portion of the first change and the second change, and estimate a sleep latency related to the object on the basis of at least a portion of the state.

In accordance with another aspect of the disclosure, an electronic device is provided. The electronic device includes: a communication circuit; and a processor, wherein the processor is configured to receive first biometric information and second biometric information on an external object measured by an external electronic device through the communication circuit, identify a first change of the first biometric information and a second change of the second biometric information, determine a state of the object related to sleep on the basis of at least a portion of the first change and the second change, and estimate a sleep latency related to the object on the basis of at least a portion of the state.

In accordance with another aspect of the disclosure, an electronic device is provided. The electronic device includes: a memory configured to store instructions; an RF sensor configured to transmit a Radio Frequency (RF) signal and receive a reflection signal of the RF signal; and one or more processors coupled to the RF sensor and the memory and configured to execute the stored instructions in order to identify one or more signals indicating a state of a user within the received reflection signal, monitor a change (difference) in data determined on the basis of the one or more signals according to a time, determine that a time point at which the user actually begins sleeping is a time point at which the monitored change is smaller than a first reference value, determine that a time point at which the user intends to sleep is a second time point at which the monitored change is larger than a second reference value, determine that a sleep latency of the user is a time interval between the first time point and the second time point, and store information on the determined time interval.

In accordance with another aspect of the disclosure, a method of an electronic device is provided. The method includes: acquiring first biometric information and second biometric information through a biometric signal detection sensor of the electronic device; identifying a first change of the first biometric information and a second change of the second biometric information; determining a state of an object related to sleep on the basis of at least a portion of the first change and the second change; and estimating a sleep latency related to the object.

In accordance with another aspect of the disclosure, a method of an electronic device is provided. The method includes: receiving first biometric information and second biometric information on an external object measured by an external electronic device through a communication circuit of the electronic device; identifying a first change of the first biometric information and a second change of the second biometric information; determining a state of an object related to a sleep on the basis of at least a portion of the first change and the second change; and estimating a sleep latency related to the object on the basis of at least a portion of the state.

In accordance with another aspect of the disclosure, a method of an electronic device is provided. The method includes: transmitting a Radio Frequency (RF) signal; receiving a reflection signal of the RF signal; identifying one or more signals indicating a state of a user within the received reflection signal; monitoring a change (difference) in data determined on the basis of the one or more signals according to a time; determining that a time point at which the user actually begins sleeping is a first time point at which the monitored change is smaller than a first reference value; determining that a time point at which the user intends to sleep is a second time point at which the monitored change is larger than a second reference value; determining that a sleep latency of the user is a time interval between the first time point and the second time point; and storing information on the determined time interval.

Advantageous Effects of Invention

An electronic device and a method of operating the same according to various embodiments can acquire information on a parameter related to sleep of a user without any independent user input for measuring a sleep state of the user.

BEST MODE FOR CARRYING OUT THE INVENTION

Figure 1:
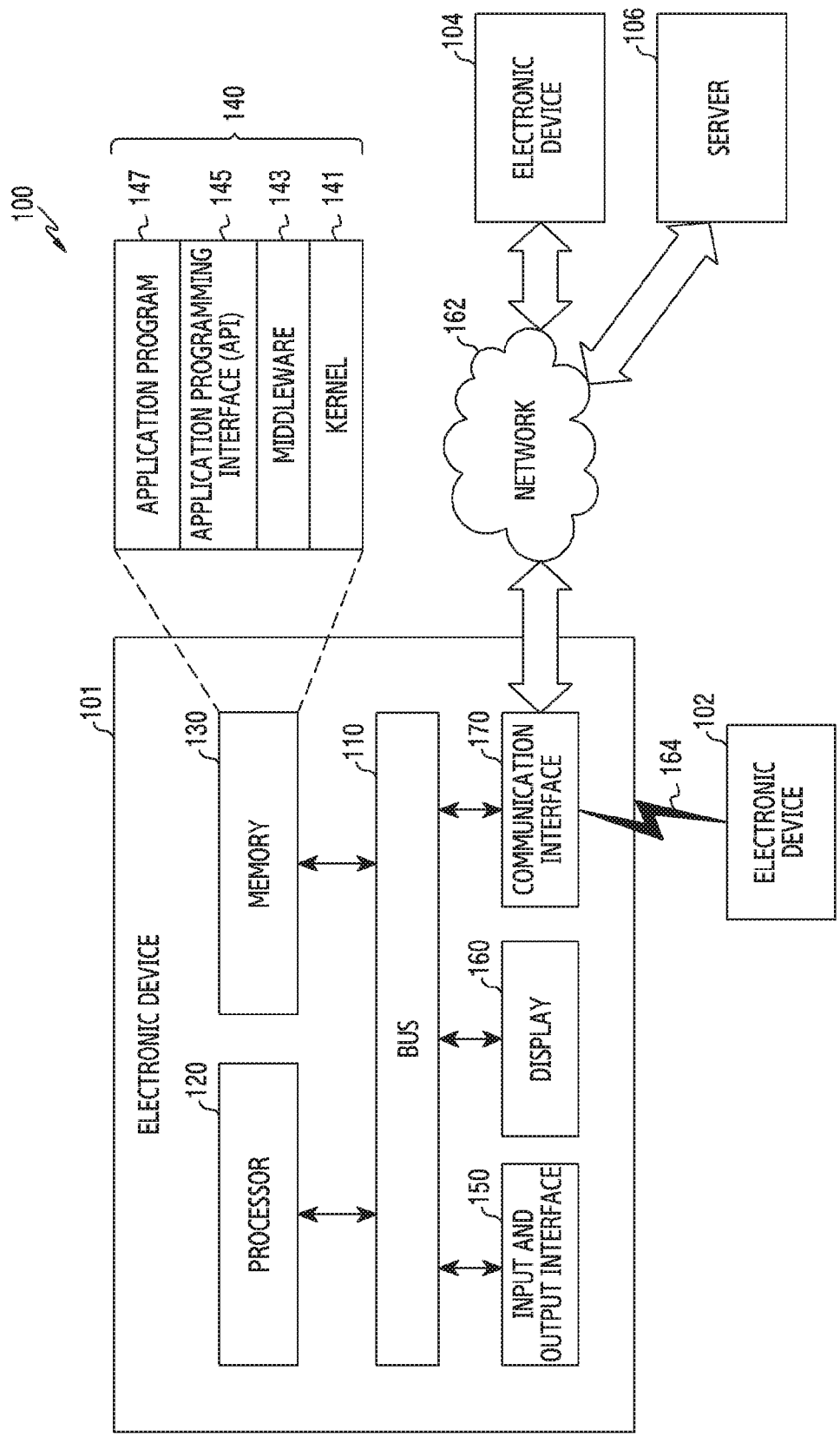
FIG. 1 illustrates an example of a network environment including an electronic device according to various embodiments.

Hereinafter, various embodiments of the present disclosure are disclosed with reference to the accompanying drawings. However, it should be understood that it is not intended to limit various embodiments of the present disclosure to a particular form but, on the contrary, the intention is to cover various modifications, equivalents, and/or alternatives of the embodiments of the present disclosure. In relation to descriptions of the drawings, like reference numerals can be used for similar components. A singular form can include a plurality of forms unless it is explicitly differently represented. In the disclosure, an expression such as "A or B", or "at least one of A or/and B" can include any and every combination of items listed together. Expressions such as "first," "second," "primarily," or "secondary" used in various embodiments can represent various elements regardless of order and/or importance and do not limit corresponding elements. Such expressions are used for distinguishing one element from another element. When an element (e.g., a first element) is "operatively or communicatively coupled with/to" or "connected to" another element (e.g., a second element), it should be understood that the element can be directly connected to the another element or can be connected to the another element through other element (e.g., a third element).

An expression "configured to (or set)" used in the present disclosure can be replaced with, for example, "suitable for," "having the capacity to," "designed to," "adapted to," "made to," or "capable of" according to a situation. In some situation, an expression "apparatus configured to" can mean that the apparatus "can" operate together with another apparatus or other components. For example, "a processor configured (or set) to perform A, B, and C" can be a dedicated processor (e.g., an embedded processor) for performing a corresponding operation or a generic-purpose processor (e.g., a Central Processing Unit (CPU) which can perform a corresponding operation by executing one or more software programs stored in a memory device.

An electronic device according to various embodiments of the present disclosure can include, for example, at least one of a smart phone, a tablet Personal Computer (PC), a mobile phone, a video phone, an e-book reader, a desktop PC, a laptop PC, a netbook computer, a workstation, a sever, a Personal Digital Assistant (PDA), a Portable Multimedia Player (PMP), an MPEG 3 (MP3) player, a mobile medical equipment, a camera, and a wearable device. The wearable device can include at least one of an accessory type (e.g., a watch, a ring, a bracelet, an ankle bracelet, a necklace, glasses, a contact lens, or a Head-Mounted-Device (HMD)), a fabric or clothing embedded type (e.g., electronic garments), a body attachable type (e.g., a skin pad or a tattoo), and an implantable circuit. In some embodiments, the electronic device can be a smart home appliance. The smart home appliance can include at least one of, for example, a television, a Digital Video Disk (DVD) player, an audio device, a refrigerator, an air-conditioner, a cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™, PlayStation™), an electronic dictionary, an electronic key, a camcorder, and an electronic frame.

In another embodiment, the electronic device can include at least one of various medical devices (e.g., various portable medical measuring devices (a blood sugar measuring device, a heartbeat measuring device, a blood pressure measuring device, or a body temperature measuring device), a Magnetic Resonance Angiography (MRA) device, a Magnetic Resonance Imaging (MRI) device, a Computed Tomography (CT) device, a scanning machine, and an ultrasonic wave device), a navigation device, a Global Navigation Satellite System (GNSS), an Event Data Recorder (EDR), a Flight Data Recorder (FDR), a vehicle infotainment device, electronic equipment for ship (e.g., a navigation device for ship and gyro compass), avionics, a security device, a head unit for a vehicle, an industrial or home robot, an Automated Teller Machine (ATM) of a financial institution, a Point Of Sales (POS) device of a store, and an Internet of Things (IoT) device (e.g., a light bulb, various sensors, electricity or gas meter, a sprinkler device, a fire alarm, a thermostat, a street light, a toaster, sports equipment, a hot water tank, a heater, and a boiler). According to an embodiment, the electronic device can include at least one of a portion of furniture or building/construction, an electronic board, an electronic signature receiving device, a projector, and various measuring devices (e.g., water supply, electricity, gas, or electric wave measuring device). According to various embodiments, the electronic device can be a flexible electronic device or a combination of two or more of the foregoing various devices. An electronic device according to embodiments of the present disclosure is not limited to the foregoing devices. The term "user", as used herein, can refer to a person using an electronic device or a device using an electronic device (e.g., an artificial intelligence electronic device).

FIG. 1 illustrates a network environment including an electronic device according to various embodiments of the disclosure.

Referring to FIG. 1, an electronic device 101 may include a bus 110, a processor 120, a memory 130, an input/output interface 150, a display 160, and a communication interface 170. In an embodiment, the electronic device 101 can omit at least one of the components or further include an additional component.

The bus 110 can include a circuit for connecting the components 120 through 170 and delivering communication signals (e.g., control messages or data) between the components 120 through 170.

The processor 120 may include one or more of a central processing unit, an application processor, and a Communication Processor (CP). The processor 120 may carry out, for example, calculation or data processing relating to control and/or communication of at least one other component of the electronic device 101.

The memory 130 can include a volatile and/or nonvolatile memory. The memory 130, for example, can store commands or data relating to at least other component of the electronic device 101. According to an embodiment, the memory 130 can store software and/or a program 140. The program 140 can include a kernel 141, middleware 143, an Application Programming Interface (API) 145, and/or an application program (or "application") 147. At least some of the kernel 141, the middleware 143, and the API 145 may be referred to as an operating system. The kernel 141 can control or manage system resources (e.g., the bus 110, the processor 120, or the memory 130) used for performing operations or functions implemented by the other programs (e.g., the middleware 134, the API 145, or the application program 147). Additionally, the kernel 141 can provide an interface for controlling or managing the system resources by accessing an individual component of the electronic device 101 from the middleware 143, the API 145, or the application program 147.

The middleware 143, for example, can serve an intermediary role for exchanging data between the API 145 or the application program 147 and the kernel 141 through communication. Also, the middleware 143 can process one or more job requests received from the application program 147, based on their priority. For example, the middleware 143 can assign a priority for using the system resource (e.g., the bus 110, the processor 120, or the memory 130) of the electronic device 101 to at least one of the application programs 147 and process the one or more job requests. The API 145, as an interface through which the application 147 controls a function provided from the kernel 141 or the middleware 143, can include, for example, at least one interface or function (e.g., an instruction) for file control, window control, image processing, or character control. The input/output interface 150, for example, can serve as an interface for delivering commands or data inputted from a user or another external device to other component(s) of the electronic device 101. Also, the input/output interface 150 can output commands or data inputted from the other component(s) of the electronic device 101 to the user or another external device.

The display 160, for example, can include a Liquid Crystal Display (LCD), a Light Emitting Diode (LED) display, an Organic Light Emitting Diode (OLED) display, a Micro Electro Mechanical Systems (MEMS) display, or an electronic paper display. The display 160, for example, can display various contents (e.g., texts, images, videos, icons, or symbols) to the user. The display 160 can include a touch screen, for example, and receive touch, gesture, proximity, or hovering inputs by using an electronic pen or a user's body part. The communication interface 170, for example, can set a communication between the electronic device 101 and an external device (e.g., a first external electronic device 102, a second external electronic device 104, or a server 106). For example, the communication interface 170 can communicate with the external device (e.g., the second external electronic device 104 or the server 106) over a network 162 using wireless communication or wired communication.

The wireless communication, for example, can at least one of Long-Term Evolution (LTE), LTE-Advanced (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. According to an embodiment, like an element 164 illustrated in FIG. 1, the wireless communication may include, for example, at least one of Wi-Fi, Li-Fi (Light Fidelity), Bluetooth, Bluetooth Low Energy (BLE), ZigBee, Near Field Communication (NFC), magnetic secure transmission, Radio Frequency (RF), and Body Area Network (BAN). According to an embodiment, the wireless communication may include a GNSS The GNSS can include, for example, Global Positioning System (GPS), Global Navigation Satellite System (GLONASS), Beidou navigation satellite system (Beidou), or Galileo (the European global satellite-based navigation system). Hereafter, the GPS can be interchangeably used with the GNSS. The wired communication, for example, can include at least one of Universal Serial Bus (USB), High Definition Multimedia Interface (HDMI), Recommended Standard 232 (RS-232), and Plain Old Telephone Service (POTS). The network 162 can include a telecommunications network, for example, at least one of a computer network (e.g., Local Area Network (LAN) or Wide Area Network (WAN)), Internet, and a telephone network.

Each of the first and second external electronic devices 102 and 104 can be of the same as or of a different type from the type of the electronic device 101. According to various embodiments, all or part of the operations executed in the electronic device 101 can be executed by one or more other electronic devices (e.g., the electronic devices 102 and 104, or the server 106). When the electronic device 101 is to perform a function or service automatically or by request, instead of or addition to performing the function or the service by the electronic device 101, the electronic device 101 can request at least part of the related function from other device (e.g., the electronic device 102 or 104, or the server 106). The other electronic device (e.g., the electronic device 102 or 104, or the server 106) can perform the requested function or an additional function and provide its result to the electronic device 101. The electronic device 101 can provide the requested function or service by processing the received result as it is or additionally. In doing so, for example, cloud computing, distributed computing, or client-server computing techniques can be used.

Figure 2:
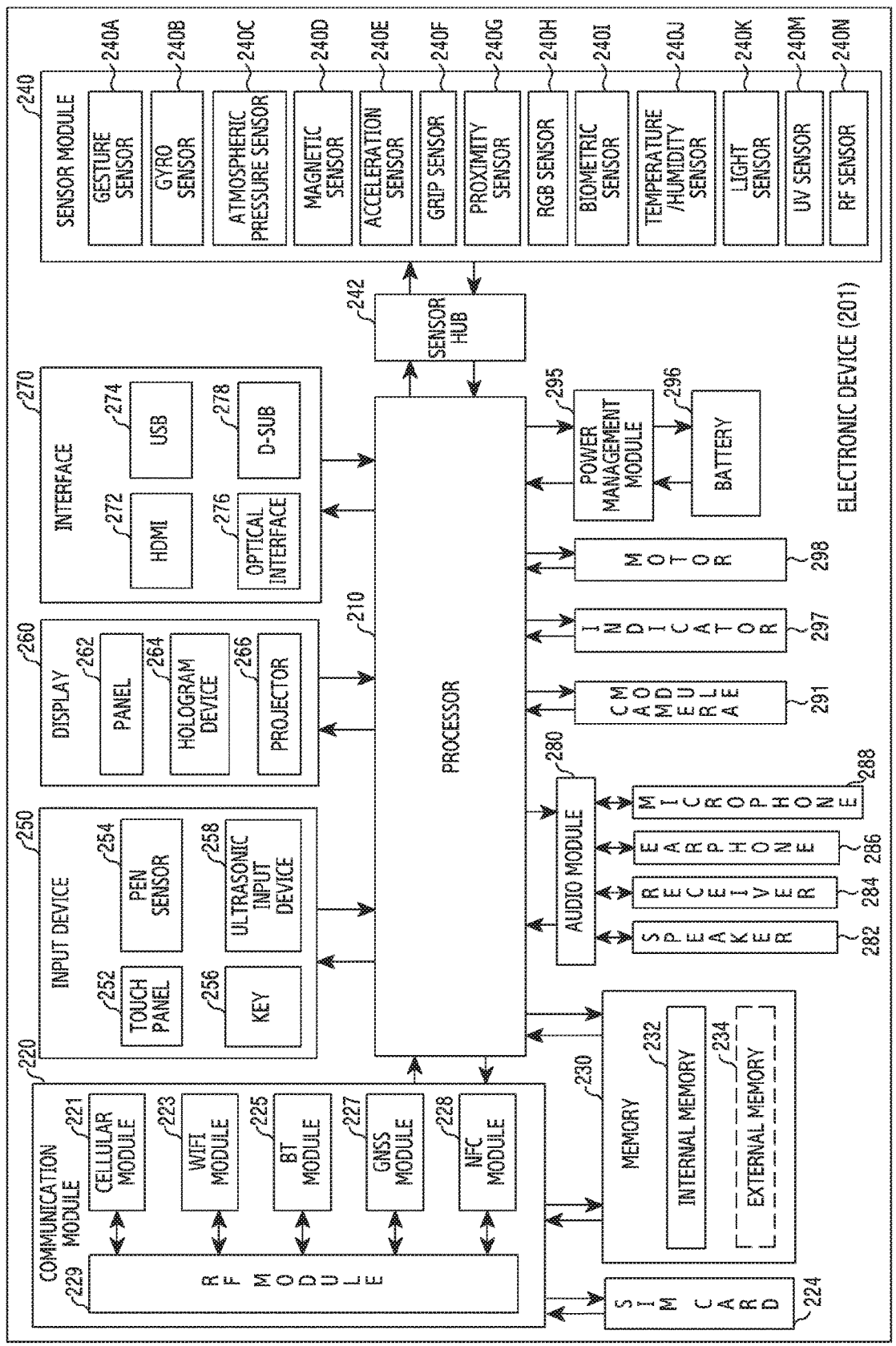
FIG. 2 is a block diagram of the electronic device according to various embodiments.

FIG. 2 is a block diagram of an electronic device according to various embodiments of the present disclosure.

The electronic device 201, for example, can include all or part of the electronic device 101 of FIG. 1. The electronic device 201 can include one or more processors (APs) 210, a communication module 220, a Subscriber Identification Module (SIM) 224, a memory 230, a sensor module 240, a sensor hub 242, an input device 250, a display 260, an interface 270, an audio module 280, a camera module 291, a power management module 295, a battery 296, an indicator 297, and a motor 298. The processor 210, for example, can control a plurality of hardware or software components connected to the processor 210 by executing an OS or an application program, and process various data and operations. The processor 210 can be implemented with, for example, a System on Chip (SoC). According to one embodiment, the processor 210 can further include a Graphic Processing Unit (GPU) and/or an image signal processor. The processor 210 may include at least part (e.g., a cellular module 221) of the components shown in FIG. 2. The processor 210 can load and process commands or data received from at least one of the other components (e.g., a nonvolatile memory) into a volatile memory, and store various data in the nonvolatile memory.

The communication module 220 can have the same or similar configuration to the communication interface 170 of FIG. 1. The communication module 220 can include, for example, a cellular module 221, a WiFi module 223, a Bluetooth (BT) module 225, a GNSS module 227 (e.g., a GPS module, a Glonass module, a Beidou module, or a Galileo module), a Near Field Communication (NFC) module 228, and a Radio Frequency (RF) module 229. The cellular module 221 can provide, for example, voice call, video call, text service, or Internet service through a communication network. According to one embodiment, the cellular module 221 can identify and authenticate the electronic device 201 in the communication network by using the SIM 224 (e.g., a SIM card). The communication module 220 may transmit or receive a D2D signal to or from at least one other electronic device. The communication module 220 may be referred to as at least one transceiver according to embodiments.

The cellular module 221 can perform at least part of a function which can be provided from the processor 210. The cellular module 221 can further include a CP. According to an embodiment, at least some (e.g., two or more) of the cellular module 221, the WiFi module 223, the BT module 225, the GNSS module 227, or the NFC module 228 can be included in one Integrated Chip (IC) or an IC package. The RF module 229 can, for example, transmit and receive communication signals (e.g., RF signals). The RF module 229 can include, for example, a transceiver, a Power Amp Module (PAM), a frequency filter, a Low Noise Amplifier (LNA), or an antenna. According to another embodiment, at least one of the cellular module 221, the WiFi module 223, the BT module 225, the GNSS module 227, or the NFC module 228 can transmit and receive RF signals through a separate RF module. The SIM 224 can include, for example, a card including a SIM and/or an embedded SIM, and contain unique identification information (e.g., an Integrated Circuit Card Identifier (ICCID)) or subscriber information (e.g., an International Mobile Subscriber Identity (IMSI)).

The memory 230 (e.g., the memory 130) can include, for example, an internal memory 232 or an external memory 234. The internal memory 232 can include at least one of, for example, a volatile memory (e.g., Dynamic Random Access Memory (DRAM), Static RAM (SRAM), or Synchronous Dynamic RAM (SDRAM)), and a non-volatile memory (e.g., One Time Programmable Read Only Memory (OTPROM), Programmable ROM (PROM), Erasable and Programmable ROM (EPROM), Electrically Erasable and Programmable ROM (EEPROM), mask ROM, flash ROM, flash memory (e.g., NAND flash or NOR flash), hard drive, or Solid State Drive (SSD)). The external memory 234 can further include a flash drive, for example, Compact Flash (CF), Secure Digital (SD), micro SD, mini SD, extreme digital (xD), or memory stick. The external memory 234 can be functionally and/or physically connected to the electronic device 201 through various interfaces.

The sensor module 240 can, for example, measure physical quantities or detect an operating state of the electronic device 201, and thus convert the measured or detected information into electrical signals. The sensor module 240, for example, can include at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a Red, Green, Blue (RGB) sensor), a bio sensor 240I, a temperature/humidity sensor 240J, an illumination sensor 240K, an Ultra Violet (UV) sensor 240M, and a radio frequency (RF) sensor 240N. Additionally or alternately, the sensor module 240 can include, for example, an E-nose sensor, an Electromyography (EMG) sensor, an Electroencephalogram (EEG) sensor, an Electrocardiogram (ECG) sensor, an InfraRed (IR) sensor, an iris sensor, and/or a fingerprint sensor. The sensor module 240 can further include a control circuit for controlling at least one sensor therein. According to an embodiment, the electronic device 201 can further include, as part of the processor 210 or individually, a processor (e.g., the sensor hub 242) configured to control the sensor module 240 and thus control the sensor module 240 while the processor 210 is sleeping.

The sensor hub 242 may receive measurement values of various sensors included in the sensor module 240 and provide the received measurement values or information determined on the basis of the measurement values to the processor 210. The sensor hub 242 may receive signals for controlling various sensors included in the sensor module 240 from the processor 210. The sensor hub 242 may control sensors on the basis of signals received from the processor 210. The sensor hub 242 may be referred to as an auxiliary processor according to embodiments.

The sensor hub 242 may operate regardless of a power state of the electronic device 201 or the processor 210. For example, the sensor hub 242 may control various sensors included in the sensor module 240 or process information received from the sensor module 240 even when the processor 210 operates in an idle state, a low power state, a sleep state, or an inactive state, The input device 250 can include, for example, a touch panel 252, a (digital) pen sensor 254, a key 256, or an ultrasonic input device 258. The touch panel 252 can use at least one of, for example, capacitive, resistive, infrared, and ultrasonic methods. Also, the touch panel 252 may further include a control circuit. The touch panel 252 can further include a tactile layer and provide a tactile response to the user. The (digital) pen sensor 254 can include, for example, part of a touch panel or a separate sheet for recognition. The key 256 can include, for example, a physical button, a touch key, an optical key, or a keypad. The ultrasonic input device 258 can detects ultrasonic waves from an input tool through a microphone (e.g., the microphone 288) and thus obtain data corresponding to the detected ultrasonic waves.

The display 260 (e.g., the display 160) can include a panel 262, a hologram device 264, or a projector 266. The panel 262 can be implemented to be, for example, flexible, transparent, or wearable. The panel 262 and the touch panel 252 can be configured as one or more module. The panel 262 can include a pressure sensor (or a force sensor) for measuring a pressure level of a user touch. The pressure sensor can be integrated with the touch panel 252, or implemented as one or more sensors separately from the touch panel 252. The hologram device 264 can show three-dimensional images in the air by using interference of light. The projector 266 can display an image by projecting light on a screen. The screen can be placed, for example, inside or outside the electronic device 201. The interface 270 can include, for example, an HDMI 272, a USB 274, an optical interface 276, or a D-subminiature (D-sub) 278. The interface 270 can be included in, for example, the communication interface 170 of FIG. 1. Additionally or alternately, the interface 270 can include, for example, a Mobile High-Definition Link (MHL) interface, a SD card/MultiMedia Card (MMC) interface, or an Infrared Data Association (IrDA) standard interface.

The audio module 280, for example, can convert sounds into electrical signals and vice versa. At least some components of the audio module 280 can be included in, for example, the input/output interface 150 of FIG. 1. The audio module 280 can process sound information input or output through, for example, a speaker 282, a receiver 284, an earphone 286, or the microphone 288. The camera module 291 is, for example, a device for capturing still images and moving images. According to one embodiment, the camera module 291 can include one or more image sensors (e.g., a front sensor or a rear sensor), a lens, an Image Signal Processor (ISP), or a flash (e.g., an LED or a xenon lamp. The power management module 295, for example, can manage the power of the electronic device 201. According to one embodiment, the power management module 295 can include a Power Management IC (PMIC), a charger IC, or a battery or fuel gauge. The PMIC can have a wired and/or wireless charging method. The wireless charging method can include, for example, a magnetic resonance method, a magnetic induction method, or an electromagnetic method, and can further include an additional circuit for wireless charging, for example, a coil loop, a resonant circuit, or a rectifier. The battery gauge, for example, can measure the remaining capacity of the battery 296, a voltage, currents, or temperature of the battery 296 during charging. The battery 296 can include, for example, a rechargeable battery and/or a solar battery.

The indicator 297 can display a specific state of the electronic device 201 or part thereof (e.g., the processor 210), for example, a booting state, a message state, or a charging state. The motor 298 can convert electrical signals into mechanical vibration and generate a vibration or haptic effect. The electronic device 201, for example, can include a processing device (e.g., a GPU) for supporting mobile TV. The processing device for supporting mobile TV, for example, can process media data according to standards such as Digital Multimedia Broadcasting (DMB), Digital Video Broadcasting (DVB), or media flow. Each of the above-described components of the electronic device can be configured with one or more components, and the name of a corresponding component can vary according to a type of an electronic device. According to various embodiments, the electronic device can be configured to omit some components, or further include an additional component. Also, some of the components of the electronic device according to various embodiments can be combined as one entity and thus identically perform the functions of the corresponding components.

Figure 3:
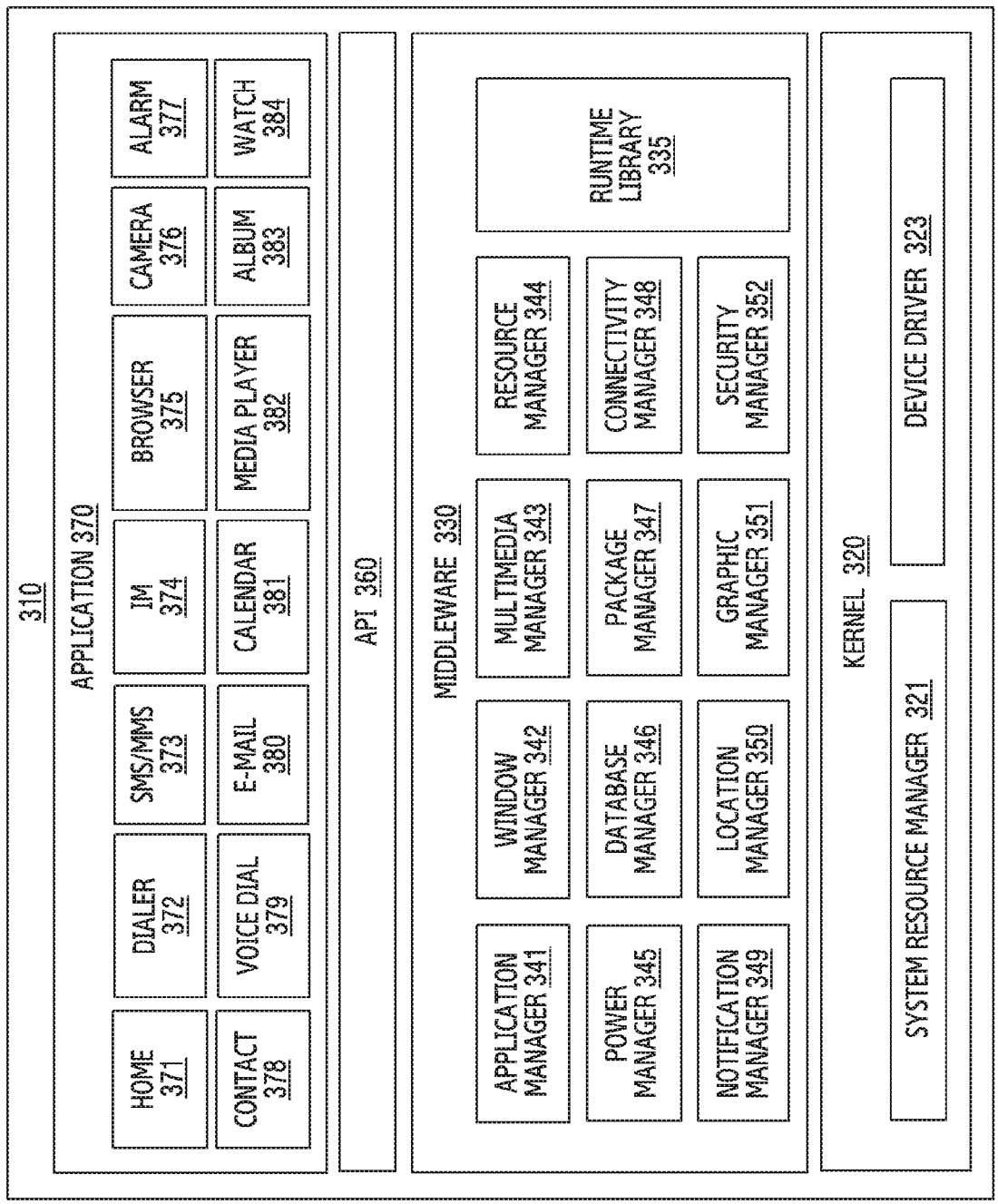
FIG. 3 is a block diagram of a program module according to various embodiments.

FIG. 3 is a block diagram of a program module according to various embodiments.

According to one embodiment, the program module 310 (e.g., the program 140) can include an OS for controlling resources relating to an electronic device (e.g., the electronic device 101, the electronic device 201) and/or various applications (e.g., the application program 147) running on the OS. The OS can include, for example, Android™, iOS™, Windows™, Symbian™, Tizen™, or Samsung Bada™ OS.

Referring to FIG. 3, The program module 310 can include a kernel 320 (e.g., the kernel 141), a middleware 330 (e.g., the middleware 143), an API 360 (e.g., the API 145), and/or an application 370 (e.g., the application 147). At least part of the program module 310 can be preloaded on the electronic device or downloaded from the external electronic device (e.g., the electronic device 102 or 104, the server 106).

The kernel 320 (e.g., the kernel 141) can include, for example, a system resource manager 321 and/or a device driver 323. The system resource manager 321 can control, allocate, or retrieve a system resource. According to one embodiment, the system resource manager 321 can include a process management unit, a memory management unit, or a file system management unit. The device driver 323 can include, for example, a display driver, a camera driver, a Bluetooth driver, a sharing memory driver, a USB driver, a keypad driver, a WiFi driver, an audio driver, or an Inter-Process Communication (IPC) driver. The middleware 330, for example, can provide a function commonly required by the application 370 or provide various functions to the application 370 through the API 360 so that the application 370 can efficiently use limited system resources inside the electronic device. According to one embodiment, the middleware 330 (e.g., the middleware 143) can include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 can include, for example, a library module used by a complier to add a new function through a programming language while the application 370 is running. The runtime library 335 can manage input/output, memory, or arithmetic function. The application manager 341, for example, can manage a life cycle of at least one of the applications 370. The window manager 342 can manage a Graphical User Interface (GUI) resource used in a screen. The multimedia manager 343 can recognize a format for playing various media files, and encode or decode a media file by using the codec of a corresponding format. The resource manager 344 can manage a source code of at least one of the application 370, and the resources such as memory or storage space. The power manager 345 can manage a capacity, a temperature of the battery or the power by operating with, for example, Basic Input/Output System (BIOS), and provide power information for the operation of the electronic device. The database manager 346 can create, search, or modify a database to be used by at least one of the application 370. The package manager 347 can manage installation or updating of an application distributed in a package file format.

The connectivity manger 348 can manage, for example, a wireless connection such as WiFi or Bluetooth. The notification manager 349 can display or notify an event such as incoming message, appointment, and proximity alert, to the user not to interrupt the user. The location manager 350 can manage location information of the electronic device. The graphic manager 351 can manage a graphic effect to be provided to the user or a user interface relating thereto. The security manager 352 can provide all security functions for system security or user authentication. According to one embodiment, when the electronic device (e.g., the electronic device 101) includes a telephone function, the middleware 330 can further include a telephony manager for managing a voice or video call function of the electronic device. The middleware 330 can include a middleware module for combining various functions of the above-described components. The middleware 330 can provide a module specialized for each type of the OS to provide a distinguished function. Also, the middleware 330 can dynamically delete part of the existing components or add new components. The API 360 (e.g., the API 145), as a set of API programming functions, can be provided as a different configuration according to the OS. For example, Android or iOS can provide one API set for each platform, and Tizen can provide two or more API sets for each platform.

The application 370 (e.g., the application program 147) can include, for example, applications of a home 371, a dialer 372, an SMS/Multimedia Messaging System (MMS) 373, an Instant Message (IM) 374, a browser 375, a camera 376, an alarm 377, a contact 378, a voice dial 379, an e-mail 380, a calendar 381, a media player 382, an album 383, a watch 384. According to various embodiments, the application 370 can include one or more applications for health care (e.g., measure an exercise amount or blood sugar level) or environmental information provision (e.g., provide air pressure, humidity, or temperature information). According to one embodiment, the application 370 can include an application (hereafter, for the understanding, referred to as an information exchange application) for supporting information exchange between the electronic device (e.g., the electronic device 101) and the external electronic device (e.g., the electronic device 102 or 104). The information exchange application can include, for example, a notification relay application for relaying specific information to the external device or a device management application for managing the external electronic device. For example, the notification relay application can forward notification information generated from another application of the electronic device to the external electronic device. Also, the notification relay application, for example, can receive and forward notification information from the external electronic device to the user. The device management application, for example, can manage (e.g., install, delete, or update) at least one function (e.g., turn-on/turn off of the external electronic device itself (or some components) or display brightness (or resolution) adjustment) of the external electronic device communicating with the electronic device, an application operating in the external electronic device, or a service provided from the external electronic device. According to one embodiment, the application 370 can include a designated application (e.g., a health care application of a mobile medical device) according to a property of the external electronic device. According to one embodiment, the application 370 can include an application received from the external electronic device. At least part of the program module 310 can be implemented with software, firmware, hardware, or a combination of at least two of them can include a module, a program, a routine, sets of instructions, or a process for executing one or more functions.

The term "module" as used in the present disclosure can imply, for example, a unit including hardware, software, firmware, or a combination of one or two or more of them. "module" can be interchangeably used with terms, for example, such as "logic", "logical block", "component", "circuit", and the like. "module" can be a minimum unit of an integral component or can be a part thereof. The "module" may be mechanically or electronically implemented and may include, for example, an application-specific integrated circuit (ASIC) chip, a field-programmable gate arrays (FPGA), or a programmable-logic device, which has been known or are to be developed in the future, for performing certain operations. At least some of devices (e.g., modules or functions thereof) or methods (e.g., operations) according to various embodiments may be implemented by instructions which are stored a computer-readable storage medium (e.g., the memory 130) in the form of a program module. The instructions, when executed by a processor (e.g., the processor 120 of FIG. 1 or the processor 210 of FIG. 2), may cause the processor to perform functions corresponding to the instructions.

The computer-readable recording medium can include a hard disk, a floppy disk, magnetic media (e.g., a magnetic tape), optical media (e.g., a CD-ROM, a DVD), magneto-optical media (e.g., a floptical disk), and hardware devices (e.g., a ROM, a RAM, or a flash memory). Also, a program instruction can include code made by a compiler or code executable by a computer using an interpreter. A module or a program module according to various embodiments can include at least one or more of the aforementioned components, omit some of them, or further include additional other components. Operations performed by a module, a program module, or other components according to various embodiments can be executed in a sequential, parallel, repetitive, or heuristic manner. In addition, some operations can be executed in a different order or be omitted, or other operations can be added.

Figure 4A:
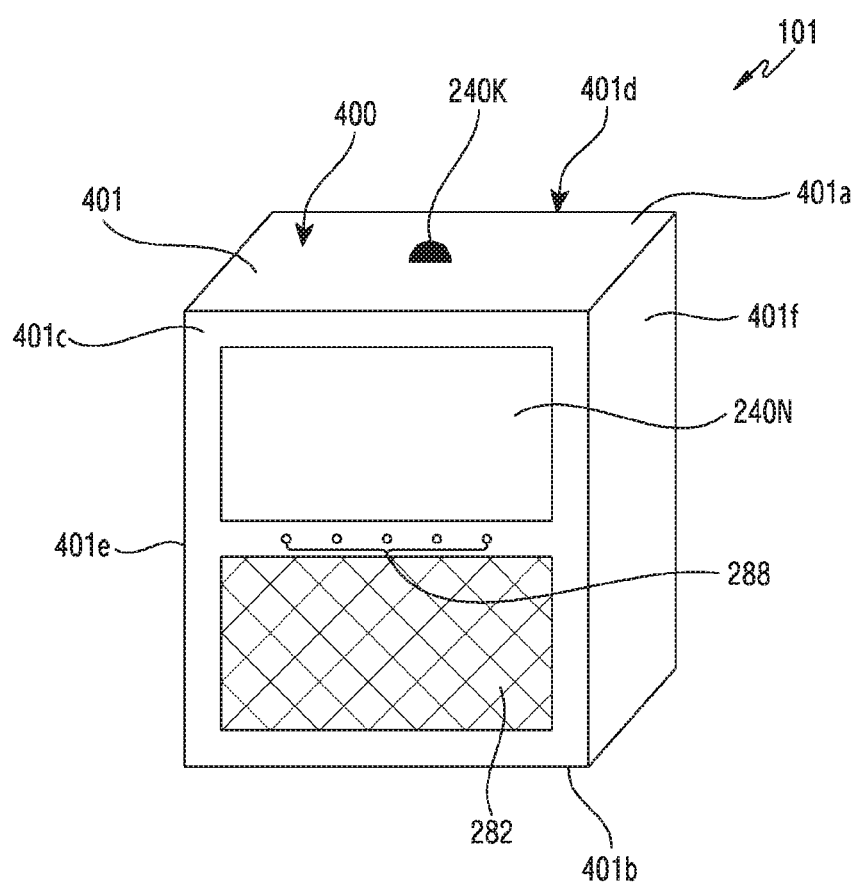
FIG. 4A illustrates an example of the structure of the electronic device according to various embodiments.

FIG. 4A illustrates an example of the structure of the electronic device according to various embodiments. Such a structure may be implemented in the electronic device 101 illustrated in FIG. 1 or the electronic device 201 illustrated in FIG. 2.

Referring to FIG. 4A, the electronic device 101 may include one or more of a housing 400, an illumination sensor 240K, a Radio Frequency (RF) sensor 240N, a speaker 282, or a microphone 288.

The housing 400 may provide a space to accommodate the element (for example, the illumination sensor 240K, the RF sensor 240N, the speaker 282, or the microphone 288). The housing 400 may be implemented in various formats. In some embodiments, the housing 400 may be implemented in the form disposed on a specific item (for example, a desktop type device) or in the form attached to a specific object (for example, a wall-mounted device). In other embodiments, the housing 400 may be implemented in a portable type (for example, a portable device) or implemented to be included in an apparatus (for example, an integrated device).

FIG. 4A illustrates an example in which the housing 400 is implemented in a hexahedral shape, but this is only for description. The housing 400 according to various embodiments may be implemented in other shapes as well as the hexahedron. For example, the housing 400 may be implemented in a hexahedral shape, a spherical shape, a cylindrical shape, or a conic shape, having one or more chambers.

The housing 400 may include a plurality of faces. For example, the housing 400 may include a top face 401a, a bottom face 401b, a front face 401c, a rear face 401d, a left face 401e, and a right face 401f.

The illumination sensor 240K may be used to measure illumination in an environment in which the electronic device 101 is located. The illumination sensor 240K may receive light in order to measure illumination in an environment in which the electronic device 101 is located. For example, the illumination sensor 240K may be configured to be included in the top face 401a or exposed to the top face 401a to receive light. FIG. 4A illustrates an example in which the illumination sensor 240K is configured on the top face 401a, but the configuration of the illumination sensor 240K is not limited thereto. For example, the illumination sensor 240K may be configured on one or more of the bottom face 401b, the front face 401c, the rear face 401d, the left face 401e, or the right face 401f.

The RF sensor 240N may acquire or detect an environment in which the electronic device 101 is located or information on a specific object within the environment through a Radio Frequency (RF) signal. According to various embodiments, the RF sensor 240N may transmit an RF signal in order to acquire, detect, or determine information on a user state. The user may be referred to as an object. The term "object" may indicate an entity having biological activity, such as a non-human animal. According to various embodiments, the RF sensor 240N may receive a signal obtained by reflection of the RF signal or a reflection signal of the RF signal in order to acquire, detect, or determine information on the user state. For example, the RF sensor 240N may be configured to be included in the front face 401c or exposed to the front face 401c in order to transmit the RF signal or receive the reflection signal of the RF signal. FIG. 4A illustrates an example in which the RF sensor 240N is configured on the front face 401c, but the configuration of the RF sensor 240N is not limited thereto. For example, the RF sensor 240N may be configured on one or more of the top face 401a, the bottom face 401b, the rear face 401d, the left face 401e, or the right face 401f.

According to embodiments, the RF sensor 240N may be referred to as a biometric signal detection sensor or a non-contact sensor.

The speaker 282 may be used to output an audio signal or a sound signal. The speaker 282 may provide a sound signal in the environment in which the electronic device 101 is located. For example, the speaker 282 may be configured to be included in the front face 401c or exposed to the front face 401c in order to output or transmit the sound signal. FIG. 4A illustrates an example in which the speaker is configured on the front face 401c, but the configuration of the speaker 282 is not limited thereto. For example, the speaker 282 may be configured on one or more of the top face 401a, the rear face 401d, the left face 401e, or the right face 401f.

The microphone 288 may be used to receive a sound signal generated or created in the environment in which the electronic device 101 is located. The microphone 288 may be configured to be included in the front face 401c or exposed to the front face 401c in order to receive or detect the sound signal. FIG. 4A illustrates an example in which the microphone 288 is configured on the front face 401c, but the configuration of the microphone 288 is not limited thereto. For example, the microphone 288 may be configured on one or more of the top face 401a, the bottom face 401b, the rear face 401d, the left face 401e, or the right face 401f. According to some embodiments, the microphone 288 may be implemented in a microphone array format including a plurality of microphones as illustrated in FIG. 4A in order to differently configure a reception gain of the sound signal according to a direction.

Figure 4B:
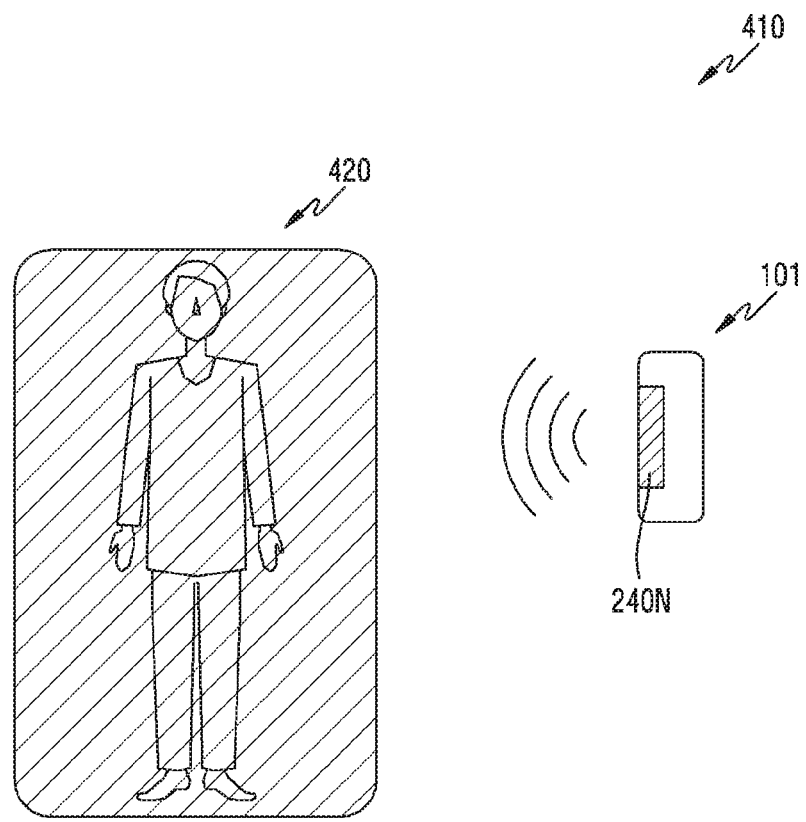
FIG. 4B illustrates an example of an environment including the electronic device according to various embodiments.

FIG. 4B illustrates an example of an environment including an electronic device according to various embodiments. The environment may include the electronic device 101 illustrated in FIG. 1 or the electronic device 201 illustrated in FIG. 2.

Referring to FIG. 4B, an environment 410 may include the electronic device 101 and a designated area 420.

The electronic device 101 may include the RF sensor 240N. According to embodiments, the RF sensor 240N may be referred to as a transceiver or a non-contact sensor. According to some embodiments, the RF sensor 240N may be configured as the communication module 220 of FIG. 2.

The RF sensor 240N may be disposed around the designated area 420. For example, the RF sensor 240N may be disposed within a specific range from the designated area 420. The RF sensor 240N may be disposed to face the designated area 420. For example, the RF sensor 240N disposed on the front face 401c of the electronic device 101 may be located in a direction to the designated area 420. The RF sensor 240N may be disposed such that the coverage of the RF sensor 240N includes the designated area 420.

The RF sensor 240N may transmit or radiate an RF signal to the designated area 420. According to some embodiments, the RF sensor 240N may continuously transmit an RF signal to the designated area 420. According to other embodiments, the RF sensor 240N may transmit an RF signal to the designated area 420 in every designated period. According to an embodiment, the designated period may be configured as a fixed value. According to another embodiment, the designated period may be adaptively changed according to a mode of the electronic device 101 or a state of the environment 410.

The RF signal may be used to determine the state of the environment in which the electronic device 101 is located or the state of the user within the environment in which the electronic device 101 is located. According to some embodiments, the RF signal may be implemented in the form of a pulse wave. The RF sensor 240N may determine a state related to the electronic device 101 through the reflection signal of the RF signal.

The RF sensor 240N may distinguish the RF signal from another signal by using a Doppler effect of the RF signal or changing a frequency through which the RF signal is transmitted according to a time. For example, the RF sensor 240N may identify the RF signal and a signal reflected from the RF signal by using a Doppler effect of the RF signal or changing a frequency through which the RF signal is transmitted according to a time.

The RF sensor 240N may receive a signal generated within the environment 410. The signal generated within the environment 410 may include one or more of the signal reflected from the RF signal (or the reflection signal of the RF signal) or the signal generated by the user. For example, the signal generated within the environment 410 is a signal reflected within the environment 410, and may include a reflection signal converted from the RF signal on the basis of a user speech or voice, a reflection signal converted from the RF signal on the basis of user action, a reflection signal converted from the RF signal on the basis of user breath, a signal converted from the RF signal on the basis of user pulse, and a signal converted from the RF signal on the basis of user heartbeat. In other words, the RF sensor 240N may receive a signal reflected from the user or the object located within the designated area 420 or converted from the RF signal.

The designated area 420 may be associated with acquisition of information or data. The designated area 420 may be a space in which the electronic device 101 acquires information or data. The designated area 420 may be a space in which the user is located. The designated area 420 may be a destination of the RF signal transmitted from the RF sensor 420N. The designated area 420 may be a space in which the reflection signal of the RF signal is generated.

The designated area 420 may be associated with sleep. The designated area 420 may be a space provided to the user for sleep. For example, the user may fall asleep within the designated area 420. For example, the designated area 420 may correspond to an area in which a bed for the user is disposed.

FIG. 4B illustrates an example in which the designated area 420 is configured in a rectangular shape having chamber-type edges, but this is only for convenience of description. According to embodiments, it should be noted that the designated area 420 is implemented in various shapes such as an oval, a triangle, and a square.

According to various embodiments, the RF sensor 240N may radiate, transmit, or output the RF signal to the designated area 420. The RF sensor 240N may receive a reflection signal converted from the RF signal. The conversion from the RF signal may be caused by the designated area 420 or an object (for example, the user) within the designated area 420.

As described above, the electronic device 101 according to various embodiments may use the RF sensor 240 N disposed for the designated area 420 to identify, detect, or determine the sleep state of the user located within the designated area 420. The electronic device 101 according to various embodiments may use the RF sensor 240N to identify, detect, or determine the sleep state of the user located within the designated area 420 without user engagement or input.

Figure 5:
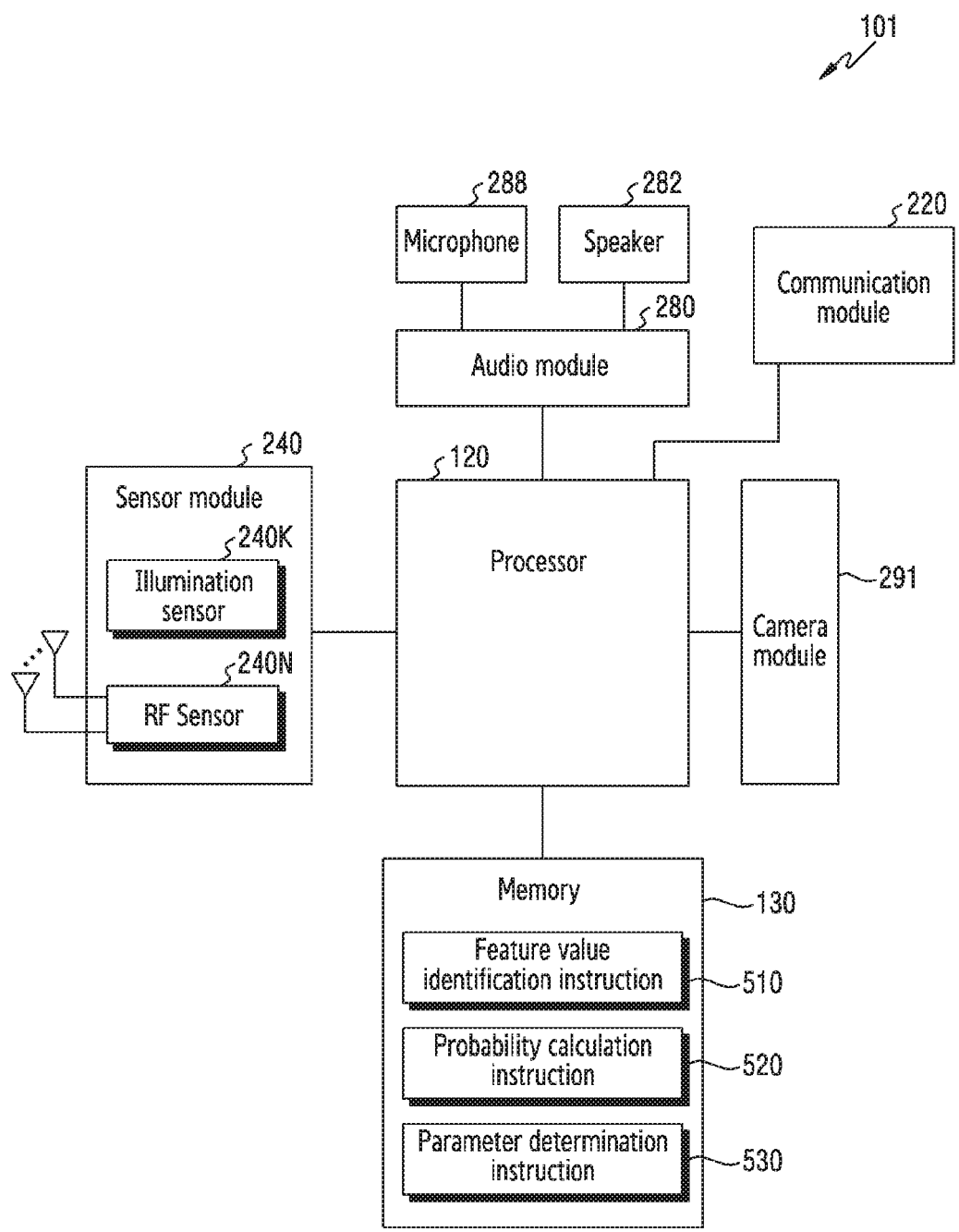
FIG. 5 illustrates an example of the functional configuration of the electronic device according to various embodiments.

FIG. 5 illustrates an example of the functional configuration of an electronic device according to various embodiments. The functional configuration may be included in the electronic device 101 illustrated in FIG. 1 or the electronic device 201 illustrated in FIG. 2.

Referring to FIG. 5, the electronic device 101 may include one or more of the processor 120, the memory 130, the communication module 220, the sensor module 240, the audio module 280, the speaker 282, the microphone 288, or the camera module 291.

The processor 120 may control the overall operation of the electronic device 101. For example, the processor 120 may control one or more of the memory 130, the communication module 220, the sensor module 240, the audio module 280, the speaker 282, the microphone 288, or the camera module 291 in order to determine the sleep state of the user. In another example, the processor 120 may control one or more of the memory 130, the communication module 220, the sensor module 240, the audio module 280, the speaker 282, the microphone 288, or the camera module 291 in order to determine sleep latency of the user on the basis of the determined sleep state of the user. In another example, the processor 120 may control one or more of the memory 130, the communication module 220, the sensor module 240, the audio module 280, the speaker 282, the microphone 288, or the camera module 291 in order to provide information on the determined sleep latency of the user. For example, the processor 120 may be an Application Processor (AP).

The processor 120 may be configured with various operation modes. According to some embodiments, the processor 120 may operate while receiving normal power (for example, receiving power higher than or equal to reference power). For example, the processor 120 may operate in a normal power mode or an active mode in which normal power is received from the electronic device 101. According to other embodiments, the processor 120 may operate while not receiving normal power (for example, receiving power lower than reference power) or while having restricted capability. For example, the processor 120 may operate in a low power mode, an idle mode, a sleep mode, or an inactive mode. When the processor 120 is configured as a plurality of processors, the processor 120 may include an auxiliary processor for controlling the sensor module 240. For example, the auxiliary processor may be the sensor hub 242. The sensor hub 242 included in the processor 120 may normally operate in a low power state. For example, even though at least some of the plurality of processors included in the processor 120 operate in the low power mode (or the idle mode, the sleep mode, or the inactive mode), the sensor hub 242 included in the processor 120 may operate in the normal mode or the active mode.

According to various embodiments, the processor 120 may control the RF sensor 240N to transmit the RF signal. For example, the processor 120 may be configured to execute instructions stored in the memory 130 in order to transmit the RF signal. The RF signal may be a reference signal for determining a state of an environment (for example, the environment 410 of FIG. 4B) in which the electronic device 101 is located. For example, the RF signal may be used to determine or identify whether the user is located within the environment 410. The RF signal may be a reference signal for determining the state of the user. For example, the RF signal may be used to identify one or more of a motion state, a breath state, or a pulse state of the user located within the environment 410. The RF signal may be configured in a format having a pulse waveform or successive waveforms.

According to various embodiments, the processor 120 may transmit the RF signal using transmission diversity. According to some embodiments, the processor 120 may transmit the RF signal through the Doppler effect. According to other embodiments, the processor 120 may transmit the RF signal in a frequency changed according to the time.

According to other embodiments, the processor 120 may control the RF sensor 240N to transmit the RF signal in every designated period. According to an embodiment, the designated period may be a fixed value.

According to another embodiment, the designated period may be adaptively changed according to the state of the electronic device 101 or the state of the environment 410 in which the electronic device 101 is located. For example, the processor 120 may control the RF sensor 240N to transmit the RF signal in every designated period (hereinafter, referred to as a first designated period) having a first length when the electronic device 101 does not determine or identify that the user is located within the designated area 420 in the environment 410 and control the RF sensor 240N to transmit the RF signal in every designated period (hereinafter, referred to as a second designated period) having a second length when the electronic device 101 determines or identifies that the user is located within the designated area 420 in the environment 410. When the user is not located within the designated area 420, the processor 120 may transmit the RF signal according to the first designated period longer than the second designated period in order to monitor whether the user is located within the designated area 420, thereby reducing power consumption due to transmission of the RF signal. When the user is located within the designated area 420, the processor 120 may transmit the RF signal according to the second designated period shorter than the first designated period in order to precisely monitor the state of the user located within the designated area 420. In another example, the processor 120 may change the designated period according to whether illumination measured by the illumination sensor 240K satisfies a designated condition. For example, when the illumination measured by the illumination sensor 240K is larger than or equal to a reference value, the processor 120 may transmit the RF signal according to the first designated period. In another example, when the illumination measured by the illumination sensor 240K is smaller than the reference value, the processor 210 may transmit the RF signal according to the second designated period. In other words, when the environment 410 is bright, the processor 120 may determine that the user does not intend to sleep and thus transmit the RF signal according to the first designated period in order to reduce power consumption. When the environment 410 is dark, the processor 120 may determine that the user intends to sleep and transmit the RF signal according to the second designated period in order to precisely identify the state of the user.

According to other embodiments, the processor 120 may control the RF sensor 240N to continuously or successively transmit the RF signal.

According to other embodiments, the processor 120 may transmit the RF signal through one or more beams using one or more antennas. For example, the processor 120 may transmit the RF signal through the one or more beams in a super high frequency band (mmWave, for example, 26 GHz or 60 GHz). When the processor 120 transmits the RF signal through the one or more beams, the RF sensor 240N may include an element (for example, a circuitry) for transmitting the beams. The element for transmitting beams will be described below with reference to FIGS. 6 and 7.

According to various embodiments, the processor 120 may control the RF sensor 240N to receive a reflection signal of the RF signal. The reflection signal may be signal converted from the RF signal on the basis of the state of the environment 410 or the state of the designated area 420. The reflection signal may be a signal converted or distorted from the RF signal on the basis of the state of the user located in the designated area 420. For example, the transmitted RF signal may be distorted or converted by one or more of motion of the user, breath of the user, and pulse of the user located in the designated area 420. The distorted or converted RF signal may be received by the RF sensor 240N as the reflection signal. In other words, the reflection signal may include one or more of a signal indicating the motion state of the user, a signal indicating the breath state of the user, or a signal indicating the pulse state of the user.

According to various embodiments, the processor 120 may process the received reflection signal.

According to some embodiments, the processor 120 may monitor a change in the received reflection signal. For example, the processor 120 may monitor whether the change in the reflection signal is out of a designated range. In response to monitoring that the change in the reflection signal is out of the designated range, the processor 120 may determine that the user or the object is located within the designated area 420.

According to other embodiments, the processor 120 may identify one or more signals from the received reflection signal. The processor 120 may identify one or more of the signal indicating the motion state of the user, the signal indicating the breath state of the user, or the signal indicating the pulse state of the user located within the designated area 420 from the reflection signal by filtering the received reflection signal. For the filtering, the processor 120 may control a plurality of filters (for example, a low pass filter, a high pass filter, and a band pass filter) included in the RF sensor 240N. For example, the processor 120 may identify the signal indicating a heartbeat of the user from the received reflection signal through the high pass filter included in the RF sensor 240N. In another example, the processor 120 may identify the signal indicating breath of the user from the received reflection signal through the low pass filter included in the RF sensor 240N.

The operation of identifying one or more signals may be triggered by various conditions. For example, in response to identification that the change in the reflection signal is out of the designated range, the processor 120 may identify the one or more signals from the reflection signal. In other words, the processor 120 may determine that the user is located within the designated area 420 by identifying that the change in the reflection signal is out of the designated range. In response to the determination, the processor 120 may trigger identification of the one or more signals from the reflection signal. By triggering the identification of the one or more signals in response to the determination, the processor 120 may reduce power consumption due to the identification of the one or more signals.

According to various embodiments, the processor 120 may analyze the one or more identified signals. The processor 120 may determine one or more values indicating the state of the user located in the designated area 420 on the basis of the one or more identified signals. For example, the processor 120 may acquire or determine a mean value and a median value of amplitudes (degrees or values) of the signals indicating the motion state of the user in a plurality of intervals (or epochs) having a specific length. The processor 120 may determine one or more values indicating the motion state of the user in the plurality of intervals on the basis of the acquired or determined mean value or median value. The one or more values may be referred to as feature values or processed values according to embodiments. In another example, the processor 120 may detect a plurality of peak time points from the signal indicating the breath state of the user. The processor 120 may determine one or more values indicating the breath state of the user on the basis of the interval between the plurality of detected peak time points. In another example, the processor 120 may detect a plurality of peak time points from the signal indicating the pulse state of the user. The processor 120 may determine one or more values indicating the pulse state of the user on the basis of an interval between the plurality of detected peak time points. A detailed description of the operation for analyzing the one or more signals (for example, the signal indicating the motion state of the user, the signal indicating the breath state of the user, and the signal indicating the pulse state of the user) will be made below with reference to FIGS. 15 to 18.

According to various embodiments, the processor 120 may store data on the one or more signals in the memory 130 or temporarily store the same. For example, the processor 120 may store data on the one or more signals in the memory 130 or temporarily store the same in order to determine a time point at which the user actually begins sleeping. In another example, the processor 120 may store data on the one or more signals in the memory 130 or temporarily store the same in order to determine a time point at which the user intends to sleep. The operation for storing the data on the one or more signals in the memory 130 or temporarily store the same may be triggered by various conditions. For example, in response to monitoring that the change in the reflection signal is out of the designated range, the processor 120 may store the data on the one or more signals in the memory 130 or temporarily store the same. In another example, in response to identification of the one or more signals from the reflection signal, the processor 120 may store the data on the one or more signals in the memory 130 or temporarily store the same.

According to various embodiments, the processor 120 may determine the time point at which the user actually begins sleeping on the basis of one or more values indicating the state of the user located in the designated area 420 (for example, the motion state of the user, the breath state of the user, and the pulse state of the user). The processor 120 may determine a probability of the sleep state of the user on the basis of the one or more values. According to some embodiments, the processor 120 may determine a time point at which the size of the determined probability reaches a reference value as the time point at which the user actually begins sleeping. According to other embodiments, the processor 120 may determine a time point at which a change in the determined probability according to the time is smaller than a reference value as the time point at which the user actually begins sleeping. According to other embodiments, the processor 120 may determine a time point at which the change in the determined probability according to the time is smaller than a first reference value and the size of the determined probability reaches a second reference value as the time at which the user actually begins sleeping. A detailed description of the operation for determining the time point at which the user actually begins sleeping will be made with reference to FIGS. 15 and 19.

According to various embodiments, the processor 120 may determine the time point at which the user intends to sleep on the basis of one or more values indicating the state of the user located in the designated area 420. The processor 120 may determine a possibility of the sleep state of the user on the basis of the one or more values. According to some embodiments, the processor 120 may determine a time point at which the size of the determined probability reaches a specific value as the time point at which the user intends to sleep. According to other embodiments, the processor 120 may determine a time point at which a change in the determined probability according to the time is larger than a specific value as the time point at which the user intends to sleep. According to other embodiments, the processor 120 may determine a time point at which the change in the determined probability according to the time reaches a first specific value and the change in the determined probability according to time is smaller than a second specific value as the time at which the user intends to sleep. The operation for determining the time point at which the user intends to sleep may be triggered in response to determination of the time point at which the user actually begins sleeping. For example, in response to determination of the time point at which the user actually begins sleeping, the processor 120 may monitor or inquire about the data on the one or more signals stored in the memory 130. The processor 120 may determine the time point at which the user intends to sleep by analyzing the monitored or inquired data. A detailed description of the operation for determining the time point at which the user intends to sleep will be made with reference to FIGS. 20 and 21.

According to various embodiments, the processor 120 may determine sleep latency of the user on the basis of the determined time point at which the user intends to sleep and the determined time point at which the user actually begins sleeping. The sleep latency may indicate a time interval in which the user makes an effort to fall asleep. The sleep latency may be a parameter indicating a quality of a sleep of the user located within the designated area 420. For example, the sleep latency may be a parameter for identifying whether the user has insomnia. In another example, the sleep latency may be a parameter for monitoring whether the user is required to take sleeping pill. The processor 120 may determine a time interval from the determined time point at which the user intends to sleep to the determined time point at which the user actually begins sleeping as the sleep latency.

According to various embodiments, the processor 120 may process information on the determined sleep latency of the user. In order to use the information on the determined sleep latency of the user, the processor 120 may process the information on the sleep latency. For example, the processor 120 may store the information on the sleep latency of the user in the memory 130 or temporarily store the same. In another example, the processor 120 may transmit the information on the sleep latency of the user to another electronic device (or an external electronic device, for example, the electronic device 102, the electronic device 104, or the server 106) linked to the electronic device 101. In another example, the processor 120 may display the information on the sleep latency of the user on the display 160 or output the same through the speaker 282.

According to various embodiments, the processor 120 may provide information on the reflection signal received through the RF sensor 240N to another electronic device (for example, the electronic device 102, the electronic device 104, or the server 106). The processor 120 may control the communication module 220 to transmit the information on the reflection signal received through the RF sensor 240N to another electronic device. When the processor 120 transmits the information on the reflection signal to the other electronic device, an operation for processing the reflection signal (for example, an operation for determining initiation of a sleep of the user, an operation for determining a time point at which the user intends to sleep, an operation for determining a sleep latency of the user, and an operation for determining a sleep duration time of the user) may be performed by the other electronic device. In other words, the information on the reflection signal may be used by the other electronic device in order to process the reflection signal.

According to various embodiments, the processor 120 may change the mode of the electronic device related to sleep. According to some embodiments, the processor 120 may change the operation mode of the electronic device 101 into the sleep mode on the basis of the determination to initiate sleep by the user located within the designated area 420. The sleep mode may be a mode for activating the function of the electronic device for the user's sleep. The sleep mode may be a mode for assisting the user in maintaining sleep. According to an embodiment, the processor 120 may change the operation mode of the electronic device 101 into the sleep mode in response to the determination of the time point at which the user initiates sleep. For example, the processor 120 may change a sound signal output through the speaker 282 of the electronic device 101 in response to the determination of the time point at which the user actually begins sleeping. The changed sound signal may be related to music for assisting the user in maintaining sleep. In another example, the processor 120 may control a brightness of a lighting output by a lighting device (not shown) included in the electronic device 101 in response to the determination of the time point at which the user actually begins sleeping. In another example, the processor 120 may control the communication module 220 (for example, the cellular module 221, the Wi-Fi module 223, the BT module 225, or the NFC module 228) to transmit a signal for changing the brightness of the lighting device located within the environment 410 to the lighting device located within the environment 410 in response to the determination of the time point at which the user actually begins sleeping. The lighting device located within the environment 410 may control the brightness of output light on the basis of reception of the signal.

According to various embodiments, the processor 120 may control the illumination sensor 240K in order to measure the brightness of the environment 410. The brightness of the environment 410 measured by the illumination sensor 240K may be used to determine the state of the environment 410 or the state of the user located within the designated area 420. For example, the processor 120 may determine the state of the user located within the designated area 420 on the basis of at least some of the information on the reflection signal received through the RF sensor 240N and the information on the brightness.

According to various embodiments, the processor 120 may control the microphone 288 in order to receive a sound signal caused within the environment 410 or a sound signal caused by the user within the designated area 420. The sound signal received through the microphone 288 may be used to determine the state of the environment 410 or the state of the user located within the designated area 420. The processor 120 may analyze the received sound signal. For example, the processor 120 may determine the state of the user located within the designated area 420 on the basis of at least some of the information on the sound signal received through the microphone 288, the information on the reflection signal received through the RF sensor 240N, and the information on the brightness measured by the illumination sensor 240K.

According to various embodiments, the processor 120 may control the camera module 291 in order to acquire an image of the environment 410 or an image of the user within the designated area 420. The image acquired by the camera module 291 may be used to determine the state of the environment 410 or the state of the user located within the designated area 420. The processor 120 may analyze the acquired image. For example, the processor 120 may determine the state of the user located within the designated area 420 on the basis of at least some of the information on the image acquired through the camera module 291, the information on the sound signal received through the microphone 288, the information on the reflection signal received through the RF sensor 240N, and the information on the brightness measured by the illumination sensor 240K.

According to various embodiments, the processor 210 may control the communication module 220 in order to receive a signal from an external electronic device (for example, the electronic device 102, the electronic device 104, or the server 106). The processor 120 may control the BT module 225 within the communication module 220 to receive a signal from a wearable device which the user is wearing. The processor 120 may determine that the user is located within the designated area 420 on the basis of reception of the signal.

The memory 130 may execute instructions stored in the memory 130 on the basis of signaling with the processor 120.

The memory 130 may store instructions for determining information on the state of the environment 410 or the state of the user within the designated area 420.

According to various embodiments, the memory 130 may store one or more instructions for extracting or identifying data from one or more signals indicating the state of the user identified on the basis of the received reflection signal.

The memory 130 may include a feature value instruction 510 for identifying one or more values indicating the state of the user on the basis of the one or more signals. For example, the memory 130 may include, as the feature value identification instruction 510, one or more of an instruction for identifying a feature value indicating a motion state of the user, an instruction for identifying a feature value indicating a breath state of the user, or an instruction for identifying a feature value indicating a pulse state of the user.

The memory 130 may include a probability calculation instruction 520 for determining a probability that the user is in the sleep state on the basis of one or more feature values identified using the feature value identification instruction command 510.

The memory 130 may include a parameter determination instruction 530 for determining a sleep parameter. The sleep parameter may be a factor for determining a sleep state of the user or a sleep quality of the user. For example, the sleep parameter may be a time point at which the user actually begins sleeping, a time point at which the user intends to sleep, a sleep latency of the user, or a time for which the user continues to sleep. The memory 130 may include, as the parameter determination instruction 530, one or more of an instruction for determining the time point at which the user actually begins sleeping, the instruction for determining the time point at which the user intends to sleep, an instruction for determining the sleep latency of the user, and an instruction for determining the time for which the user continues to sleep.

The communication module 220 may be used for communication between an external electronic device (for example, the electronic device 102, the electronic device 104, or the server 106) and the electronic device 101. According to some embodiments, the communication module 220 may receive a signal from a wearable device which the user is wearing through a Bluetooth communication path or a Wi-Fi communication path. The signal may indicate that the user is located within the designated area 420. The communication module 220 may provide the received signal to the processor 120. According to other embodiments, the communication module 220 may transmit a signal to another electronic device (for example, the electronic device 102, the electronic device 104, or the server 106) linked to the electronic device 101 through a cellular communication path, a Wi-Fi communication path, or a BT communication path. The signal may include information related to the sleep of the user. For example, the signal may include information on the sleep latency of the user. In another example, the signal may include information indicating the user actually begins sleeping. In another example, the signal may include information for changing the mode of the external electronic device into a mode related to the sleep of the user.

The sensor module 240 may be used to acquire information on the state of the environment 410 or information on the state of the user located within the designated area 420. For example, the illumination sensor 240K may receive light of the environment 410 or light of the designated area 420 through a light-receiving unit. The illumination sensor 240K may provide information on the received light to the processor 120. In another example, the RF sensor 240N may transmit an RF signal or receive a reflection signal of the RF signal. The RF sensor 240N may provide information on the received reflection signal to the processor 120. According to some embodiments, the RF sensor 240N may be included in the communication module 220. For example, the RF sensor 240N may be disposed within the communication module 220, or the RF sensor 240N and the communication module 220 may be disposed as separate modules as illustrated in FIG. 5.

The audio module 280 may process a sound signal received through the microphone 288. For example, the audio module 280 may remove noise included in the voice signal received through the microphone 288 or convert the voice signal received through the microphone 288 (for example, ADC (analog-to-digital)). The audio module 280 may provide the processed voice signal to the processor 120.

The audio module 280 may process a sound signal output through the speaker 282. For example, the audio module 280 may convert a sound signal received from the processor 120.

The microphone 288 may be used to receive a voice signal caused within the environment 410 or a voice signal caused by the user located within the designated area 420. The microphone 288 may provide the voice signal received by the processor 120 through the audio module 280.

The speaker 282 may output the sound signal to the environment 410 or the designated area 420. For example, the speaker 282 may output the sound signal provided from the processor 120 through the audio module 280.

The camera module 291 may be used to acquire an image. For example, the camera module 291 may acquire an image of the user located within the designated area 420 according to a predetermined period. The acquired image may be used to analyze the sleep state of the user. The camera module 291 may include a circuit (for example, an image processor) for processing the acquired image. The camera module 291 may provide information on the acquired image to the processor 120.

As described above, the electronic device 101 according to various embodiments may determine the sleep state of the user located within the designated area 420 through the RF sensor 240N. The electronic device 101 may determine the sleep latency of the user without any intervention of the user or user input. For example, the electronic device 101 may determine that a time interval between the time point at which the user intends to sleep and the time point at which the user actually begins sleeping is the sleep latency of the user without any intervention of the user or user input. By determining the sleep latency, the electronic device 101 may provide a solution related to sleep.

Figure 6:
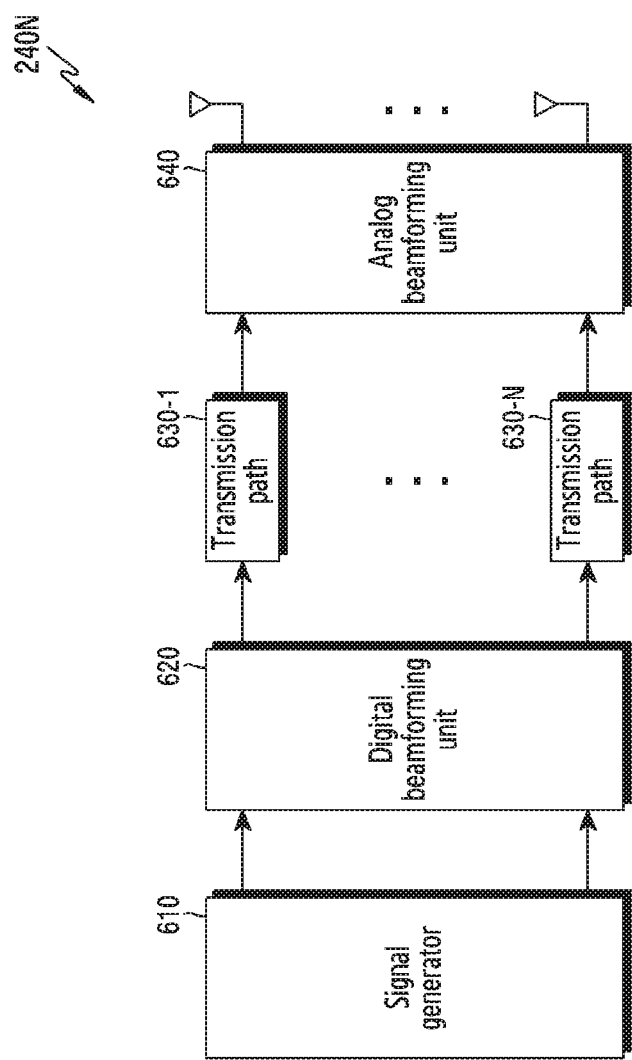
FIG. 6 illustrates an example of the functional configuration of an RF sensor according to various embodiments.

FIG. 6 illustrates an example of the functional configuration of the RF sensor according to various embodiments. The functional configuration of the RF sensor may be included in the RF sensor 240N illustrated in FIG. 5.

Referring to FIG. 6, the RF sensor 240N may include a signal generator 610, a digital beamforming unit 620, a plurality of transmission paths 630-1 to 630-N, and an analog beamforming unit 640.

The signal generator 610 may generate an RF signal. The signal generator 610 may generate an RF signal for determining the state of the user or an object located within the designated area 420. The signal generator 610 may generate the RF signal in a digital format.

The digital beamforming unit 620 may perform bemforming on the RF signal having the digital format. To this end, the digital beamforming unit 620 may multiply beamforming weighted values by digital data included in the RF signal. The beamforming weighted values may be used to change the size and phase of the signal, and may be referred to as a "precoding matrix" or a "precoder". The digital beamforming unit 620 may output the digitally beamformed RF signal to at least one of the plurality of transmission paths 630-1 to 630-N. According to some embodiments, the RF signal may be multiplexed according to a Multiple Input Multiple Output (MIMO) transmission scheme. According to other embodiments, the digital beamforming unit 620 may output the same RF signals used for a diversity gain to at least one of the plurality of transmission paths 630-1 to 630-N.

The plurality of transmission paths 630-1 to 630-N may convert digitally beamformed RF signals into analog signals. To this end, each of the plurality of transmission paths 630-1 to 630-N may include a Digital Analog Converter (DAC) and an up converter. In other words, the plurality of transmission paths 630-1 to 630-N may provide an independent signal processing process for a plurality of RF signals (or output modulation symbols) generated through the digital beamforming. According to an implementation type, some of the elements of the plurality of transmission paths 630-1 to 630-N may be used in common.

The analog beamforming unit 640 may perform beamforming on an RF signal having an analog format. To this end, the analog beamforming unit 640 may multiply beamforming weighted values by RF signals having the analog format. The beamforming weighted values may be parameters for changing the size and phase of the signals. Specifically, the analog beamforming unit 640 may be configured as illustrated in FIG. 7 according to the plurality of transmission paths 630-1 to 630-N and the connection structure between antennas.

Figure 7:
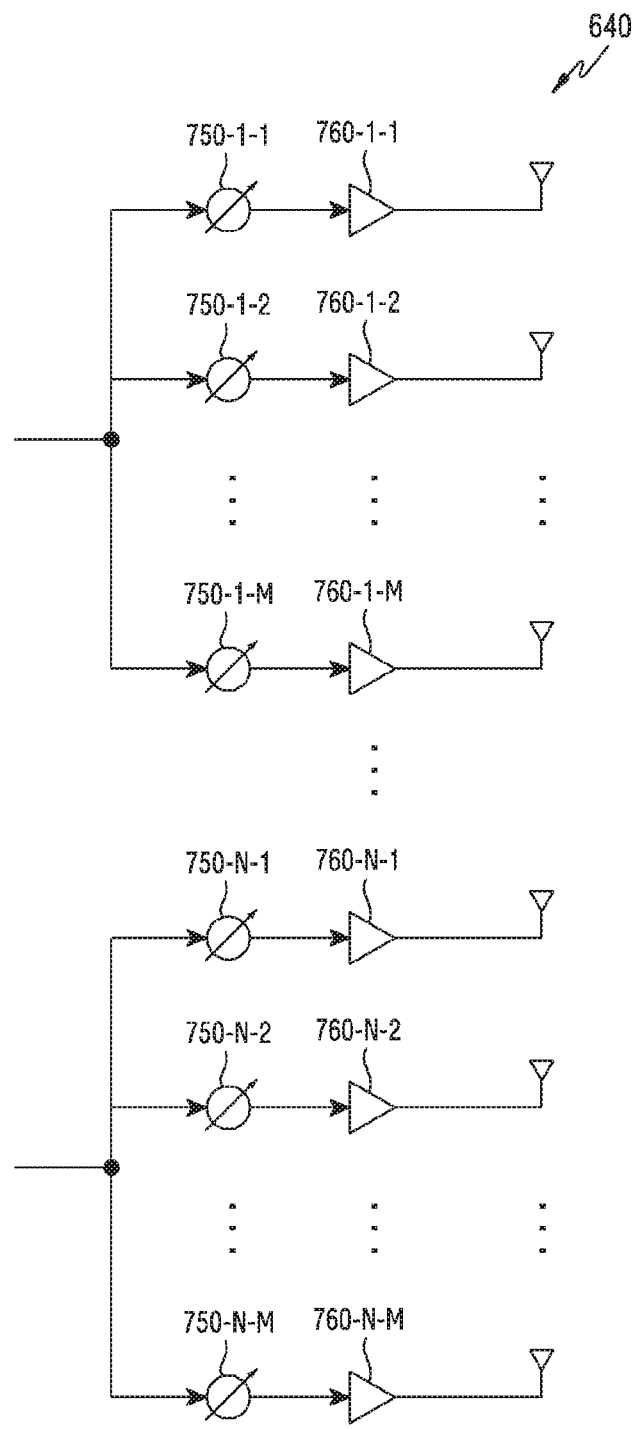
FIG. 7 illustrates an example of the functional configuration of an analog beamforming unit according to various embodiments.

FIG. 7 illustrates an example of the functional configuration of the analog beamforming unit according to various embodiments. The functional configuration may be included in the analog beamforming unit 640 of FIG. 6.

Referring to FIG. 7, signals input into the analog beamforming unit 640 may be transmitted through antennas via phase/size conversion and amplification operation. The signals of the respective paths may be transmitted through different antenna sets, that is, antenna arrays. In consideration of processing of a signal input through a first path, the signal may be converted into signal sequences having different or the same phase/size by phase/size converters 750-1-1 to 750-1-M, amplified by amplifiers 760-1-1 to 760-1-M, and then transmitted through antennas.

As described above, the electronic device according to various embodiments may include: a biometric signal detection sensor configured to acquire first biometric information and second biometric information on an object outside the electronic device; and a processor, and the processor may be configured to acquire the first biometric information and the second biometric information through the biometric signal detection sensor, identify a first change of the first biometric information and a second change of the second biometric information, determine a state of the object related to a sleep on the basis of at least a portion of the first change and the second change, and estimate a sleep latency related to the object on the basis of at least a portion of the state.

According to some embodiments, the biometric signal detection sensor may include an RF sensor, and the processor may be configured to acquire motion information of the object through the RF sensor and estimate the sleep latency on the basis of at least a portion of the first change, the second change, or the motion information.

According to other embodiments, the electronic device may further include an image sensor, and the processor may be configured to acquire image information of the object through the image sensor, acquire motion information of the object on the basis of at least a portion of the acquired image information, and estimate the sleep latency on the basis of at least a portion of the first change, the second change, or the motion information.

According to other embodiments, the first biometric information may include information on breath of the object, and the second biometric information may include information on a heart rate of the object.

The electronic device according to various embodiments may include: a communication circuit; and a processor, and the processor may be configured to receive first biometric information and second biometric information on an external object measured by an external electronic device through the communication circuit, identify a first change of the first biometric information and a second change of the second biometric information, determine a state of the object related to a sleep on the basis of at least a portion of the first change and the second change, and estimate a sleep latency related to the object on the basis of at least a portion of the state.

The electronic device according to various embodiments may include: a memory configured to store instructions; an RF sensor configured to transmit a Radio Frequency (RF) signal and receive a reflection signal of the RF signal; and one or more processors coupled to the RF sensor and the memory and configured to execute the stored instructions in order to identify one or more signals indicating a state of a user within the received reflection signal, monitor a change (difference) in data determined on the basis of the one or more signals according to a time, determine that a time point at which the user actually begins sleeping is a first time point at which the monitored change is smaller than a first reference value, determine that a time point at which the user intends to sleep is a second time point at which the monitored change is larger than a second reference value, determine that a sleep latency of the user is a time interval between the first time point and the second time point, and store information on the determined time interval.

According to some embodiments, the one or more processors may be configured to execute the stored instructions in order to monitor the received reflection signal, identify the one or more signals within the received reflection signal in response to monitoring that a change in the reflection signal is output of a predetermined range, and store the data in the memory or temporarily store the data in response to monitoring that the change in the reflection signal is output of the predetermined range. For example, the predetermined range may be configured to identify whether the user is located in a specified area. In another example, the one or more processors may be configured to execute the stored instructions in order to identify the stored data in response to the determination that the time point at which the user actually begins sleeping is the first time point, identify the second time point at which the change within the stored data is larger than the second reference value, and determine that the time point at which the user intends to sleep is the second time point.

According to other embodiments, the one or more signals may include a first signal indicating motion of the user, a second signal indicating a breath state of the user, or a third signal indicating a heartbeat state of the user. For example, the one or more processors may be configured to execute the stored instructions in order to acquire a first value indicating the motion of the user from the first signal, acquire a second value indicating the breath state of the user from the second signal, acquire a third value indicating the heartbeat state of the user from the third signal, and determine that a probability of a sleep state of the user is the data on the basis of at least a portion of the first value, the second value, and the third value.

According to other embodiments, the RF sensor may include a plurality of filters, and the one or more processors may be configured to execute the stored instructions in order to identify the first signal related to a first band within the received reflection signal through a first filter in the plurality of filters, identify the second signal related to a second band within the received reflection signal through a second filter in the plurality of filters, and identify the third signal related to a third band within the received reflection signal through a third filter in the plurality of filters.

According to other embodiments, the electronic device may further include an illumination sensor configured to measure illumination of light around the electronic device and a microphone configured to receive a sound signal around the electronic device, and the one or more processors may be further configured to execute the stored instructions in order to determine a time point at which the user actually begins sleeping on the basis of at least a portion of information on the illumination and information on the sound signal and determine a time point at which the user intends to sleep on the basis of at least a portion of the information on the illumination and the information on the sound signal.

According to other embodiments, the electronic device may further include a circuit configured to control a brightness of an environment in which the electronic device is located, and the one or more processors may be configured to further configured to execute the stored instructions in order to control the brightness of the environment in which the electronic device is located in response to the determination of the time point at which the user actually begins sleeping.

According to other embodiments, the electronic device may further include a communication interface configured to communicate with an external electronic device, and the one or more processors may be further configured to execute the stored instructions in order to transmit information on the determined time interval to the external electronic device.

According to other embodiments, the electronic device may further include a speaker configured to output a sound signal, and the one or more processors may be further configured execute the stored instructions in order to change the output sound signal in response to the determination of the time point at which the user actually begins sleeping.

According to other embodiments, the RF sensor may include a transmission circuit configured to transmit the RF signal through a plurality of beams and a plurality of antennas, and the one or more processors may be configured to execute the stored instructions in order to transmit the RF signal through the plurality of beams.

Figure 8A:
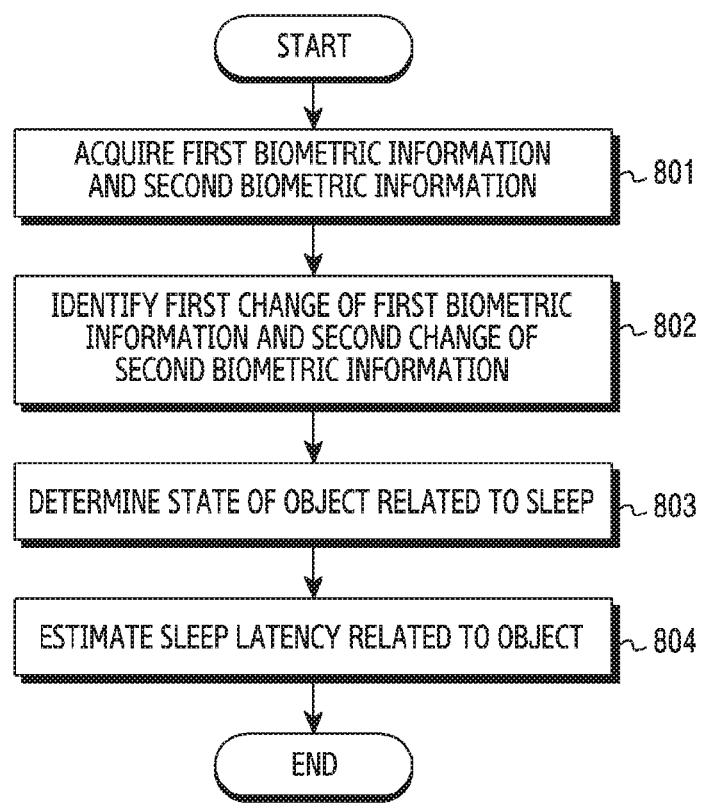
FIG. 8A illustrates an example of the operation of the electronic device according to various embodiments.

FIG. 8A illustrates an example of the operation of an electronic device according to various embodiments. The operation may be performed by the electronic device 101 illustrated in FIG. 1 or the element (for example, the processor 120) of the electronic device 101.

Referring to FIG. 8A, in operation 801, the processor 120 may acquire first biometric information and second biometric information. For example, the processor 120 may receive a reflection signal of an RF signal transmitted through the RF sensor. The processor 120 may receive the first biometric information and the second biometric information within the reflection signal. The first biometric information and the second biometric information may include data indicating the state of the environment 410 or the state of an object located with the designated area 420. For example, one or more pieces of the first biometric information and the second biometric information may include one or more pieces of data indicating a motion state of the object, data indicating a breath state of the object, or data indicating a heartbeat state of the object.

In operation 802, the processor 120 may identify a first change of the acquired first biometric information and a second change of the acquired second biometric information. For example, the processor 120 may identify whether the first biometric information and the second biometric information increase, the first biometric information and the second biometric information decrease, or the changes of the first biometric information and the second biometric information are larger than or equal to the reference size.

In operation 803, the processor 120 may determine the state of the object related to sleep on the basis of at least some of the first change and the second change. For example, the processor 120 may determine that the object is currently moving on the basis of at least some of the first change and the second change. In another example, the processor 120 may determine that the object is not currently moving on the basis of at least some of the first change and the second change. In another example, the processor 120 may determine that the heartbeat of the object is currently in a resting heart rate state on the basis of at least some of the first change and the second change. In another example, the processor 120 may identify that the breath state of the object is in a regular or uniform state on the basis of at least some of the first change and the second change.

In operation 804, the processor 120 may estimate the sleep latency related to the object on the basis of at least a portion of the state. The sleep latency may be a time interval from the time point at which the object intends to sleep to the time point at which the object actually begins sleeping. The processor 120 may identify that the state of the object is changed from the moving state to the non-moving state, that the heartbeat state of the object is changed to the resting heart rate state, or that the breath state of the object is changed to the regular state on the basis of at least a portion of the state. The processor 120 may estimate the sleep latency related to the object on the basis of the identification.

Figure 8B:
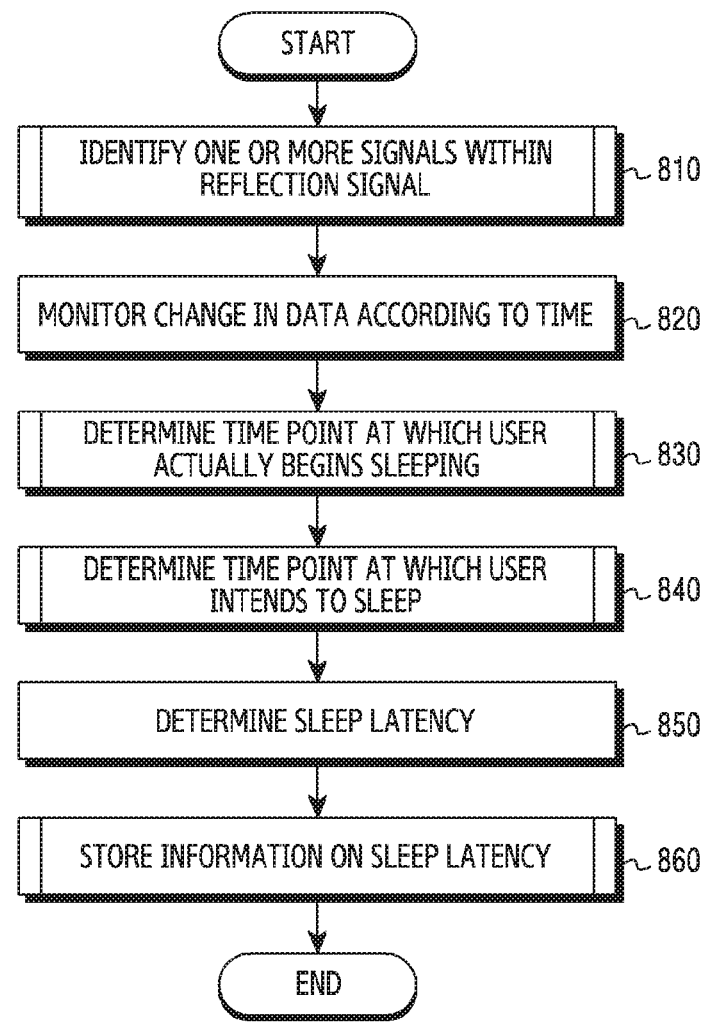
FIG. 8B illustrates another example of the operation of the electronic device according to various embodiments.

FIG. 8B illustrates another example of the operation of the electronic device according to various embodiments. The operation may be performed by the electronic device 101 illustrated in FIG. 1 or the element (for example, the processor 120) of the electronic device 101.

Referring to FIG. 8B, in operation 810, the processor 120 may identify one or more signals within a reflection signal. The reflection signal may be a reflection signal of an RF signal transmitted by the RF sensor 240N. One or more signals included in the reflection signal may indicate the state of the environment 410 or the state of the user or the object located within the designated area 420. For example, the one or more signals may include one or more of a signal indicating a motion state of the user, a signal indicating a breath state of the user, or a signal indicating a heartbeat state of the user. The processor 120 may identify the one or more signals within the reflection signal through a plurality of filters included in the RF sensor 240N of the electronic device 101.

According to some embodiments, when the RF sensor 240N does not include a plurality of filters, the processor 120 may receive information on the reflection signal from the RF sensor 240N. The processor 120 may identify or extract information on the one or more signals from the received information on the reflection signal.

According to some embodiments, the processor 120 may identify the one or more signals within the reflection signal in response to monitoring that a change in the reflection signal is output of a predetermined range. In other words, the processor 120 may trigger the identification of the one or more signals within the reflection signal in response to monitoring that the change in the reflection signal is output of the predetermined range. By performing the operation of monitoring the change in the reflection signal before the operation of identifying the one or more signals within the reflection signal, the processor 120 may save power consumed by the determination of the state of the environment 410 or the state of the user located within the designated area 420.

In operation 820, the processor 120 may monitor a change in data determined on the basis of the one or more identified signals according to the time. The data may be a value indicating the state of the user located within the environment 410 or the designated area 420. The state of the user may be relevant to the sleep of the user. For example, the data may be determined on the basis of at least one of one or more values (hereinafter, a first value) indicating the motion state of the user, one or more values (hereinafter, a second value) indicating the breath state of the user, or one or more values (hereinafter, a third value) indicating the heartbeat state of the user. For example, the data may be a probability indicating the sleep state of the user determined on the basis of one or more of the first value, the second value, or the third value. The probability may indicate a possibility of the sleep state of the user. A minimum value of the probability may be 0% (percent), and a maximum value of the probability may be 100%. For example, when the determined probability is a %, the possibility of the sleep state of the user may be higher than the possibility of the sleep state of the user in the case in which the probability is b % smaller than a %. The processor 120 may monitor or identify a change in the determined probability according to the time in real time.

In operation 830, the processor 120 may determine a time point at which the user actually begins sleeping. The processor 120 may determine the time point at which the user actually begins sleeping as a time point at which the monitored change in the data according to the time is smaller than a first reference value. The first reference value may be used to determine how much the state of the user related to sleep is stable. The first reference value may be used to determine whether the user actually begins sleeping. According to embodiments, the first reference value may be a fixed value or may be an adaptively changed value. For example, the first reference value may be adaptively changed for each place in which the electronic device 101 is located, for each user using the electronic device 101, or each time period during which the electronic device 101 operates on the basis of machine learning of the electronic device 101 or machine learning of another electronic device linked to the electronic device 101 through communication. Since the data may be relevant to the probability, the large change in the data according to the time may indicate that the user is highly likely to conduct an action other than sleep. The processor 120 may determine whether the user actually begins sleeping by monitoring the time point at which the change in the data according to the time is smaller than the first reference value.

According to some embodiments, the processor 120 may determine the time point at which the user actually begins sleeping in further consideration of the absolute size of the data. For example, when the monitored change in the data according to the time is smaller than the first reference value but the absolute size of the data is larger than or equal to a threshold value, the processor 120 may determine that the user does not actually begin sleeping. In this case, the processor 120 may determine that the time point at which the absolute size of the data is smaller than the threshold value and the change in the data according to the time is smaller than the first reference value is the time point at which the user actually begins sleeping. A detailed description of operation 830 will be made below with reference to FIGS. 15 to 19.

In operation 840, the processor 120 may determine the time point at which the user intends to sleep. The processor 120 may determine that the time point at which the user intends to sleep is a second time point at which the monitored change in the data according to the time is larger than a second reference value. The second reference value may be used to determine how much the state of the user related to sleep is changed. The second reference value may be used to determine how much the probability of the sleep state of the user increases. According to embodiments, like the first reference value, the second reference value may be a fixed value or an adaptively changed value. Since the data may be relevant to the probability, the rapid increase in the change in the data according to the time may be associated with the time point at which the user intends to sleep. The processor 120 may determine whether the user intends to sleep by monitoring the time point at which the change in the data according to the time is larger than the second reference value.

According to some embodiments, the processor 120 may determine that a time point at which a maximum increase among the changes in the data according to the time within a predetermined (or specified) time interval before the determined time point at which the user actually begins sleeping is the time point at which the user intends to sleep. To this end, the processor 120 may control the memory 130 to store information related to the data in response to operation 810 or 820.

A detailed description of operation 840 will be made below with reference to FIGS. 15 to 19.

FIG. 8 illustrates that the processor 120 performs operation 840 after operation 830, but this is only for convenience of description. Operations 840 and 830 may be performed in parallel, or in reverse order. For example, after determining that the time point at which the change in the data according to the time is larger than the second reference value is the time point at which the user intends to sleep, the processor 120 may determine that the time point at which the change in the data according to the time is smaller than the first reference value is the time point at which the user actually begins sleeping. In another example, after storing information on the change in the data according to the time, the processor 120 may determine the time point at which the user intends to sleep and the time point at which the user actually begins sleeping by analyzing the stored information. In another example, the processor 120 may store the information on the data with a triggering condition of operation 810 or operation 820. The processor 120 may determine the time point at which the user actually begins sleeping while the information on the data is stored. The processor 120 may determine the time point at which the user intends to sleep on the basis of the stored information with a triggering condition of the determination of the time point at which the user actually begins sleeping.

In operation 850, the processor 120 may determine or estimate the sleep latency of the user. The sleep latency may be a time interval between the time point at which the user intends to sleep and the time point at which the user actually begins sleeping.

In operation 860, the processor 120 may store information on the determined sleep latency. The processor 120 may store the information on the determined sleep latency in the memory 130 or temporarily store the information in a buffer. According to some embodiments, the processor 120 may store the information on the sleep latency in the memory 130 or temporarily store the information in order to provide the information on the sleep latency to another electronic device (for example, the electronic device 102, the electronic device 104, or the server 106). According to other embodiments, the processor 120 may store the information on the sleep latency in the memory 130 or temporarily store the information in order to transfer the information on the sleep latency (for example, display or output the information on the sleep latency) to the user.

FIG. 8 illustrates that the processor 120 included in the electronic device 101 performs operations 810 to 860, but this is only convenience for description. The processor 120 of the electronic device 101 according to various embodiments may control the communication module 220 to transmit information (for example, information related to the data) on the reflection signal related to the RF signal transmitted through the RF sensor 240N to another electronic device (for example, the electronic device 102, the electronic device 104, or the server 106). In this case, at least some of operations 810 to 860 may be performed by another electronic device (for example, the electronic device 102, the electronic device 104, or the server 106) receiving the information on the reflection signal.

Although FIG. 8 illustrates the operation in which the processor 120 of the electronic device 101 according to various embodiments acquires or determines the information related to the sleep of the user on the basis of the information acquired by the RF sensor 240N, the processor 120 may acquire or determine the information related to the sleep of the user further on the basis of information received through other sensing devices (for example, the illumination sensor 240K, the camera module 291, and the microphone 288) included in the electronic device 101.

As described above, the electronic device 101 according to various embodiments may acquire information on the parameter related to the sleep of the user by just including the RF sensor 240N without any independent user input for measuring the sleep state of the user. For example, the electronic device 101 may determine the sleep latency of the user without any user input on the basis of the reflection signal received through the RF sensor 240N.

Figure 9:
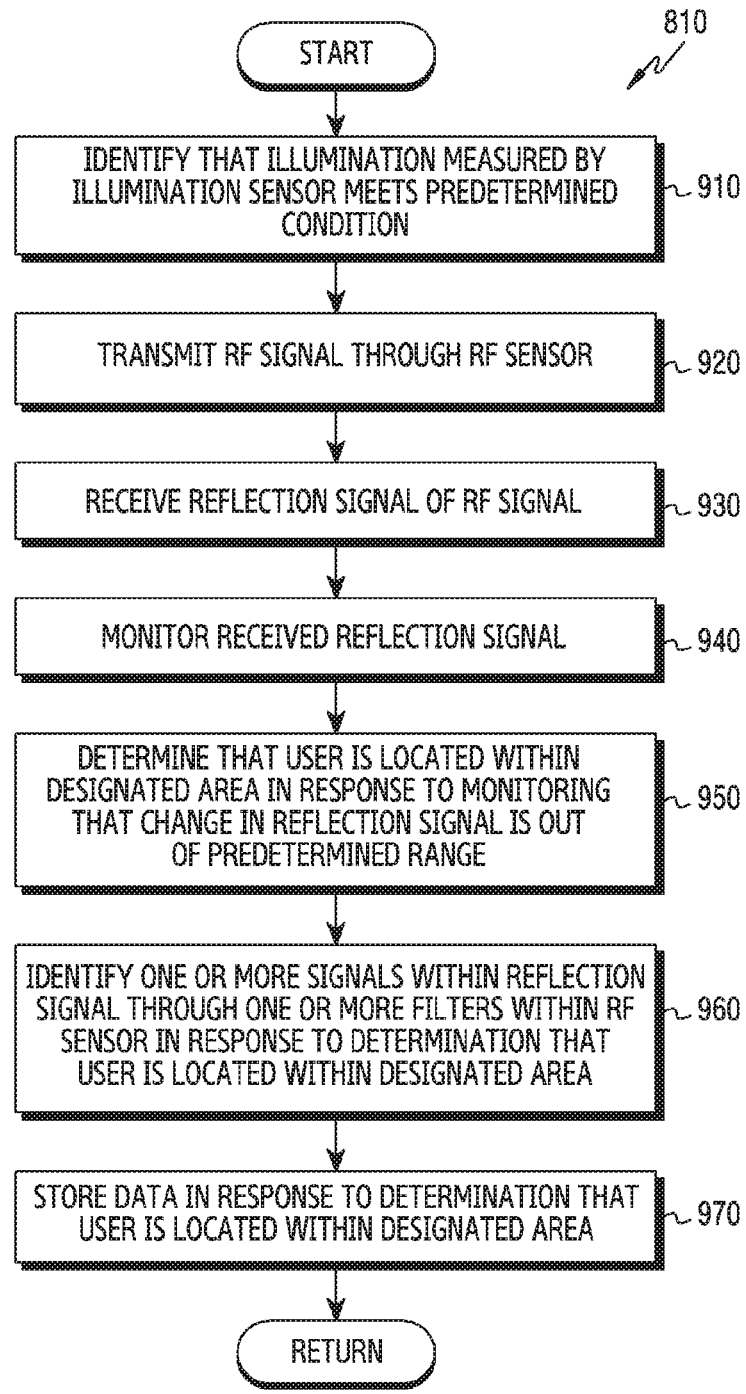
FIG. 9 illustrates an example of the operation of the electronic device for identifying one or more signals within the reflection signal according to various embodiments.

FIG. 9 illustrates an example of the operation of the electronic device for identifying one or more signals within the reflection signal according to various embodiments. The operation of the electronic device may be performed by the electronic device 101 illustrated in FIG. 1 or an element (for example, the processor 120) included in the electronic device 101.

In FIG. 9, operations 910 to 970 may be relevant to operation 810 of FIG. 8.

Referring to FIG. 9, in operation 910, the processor 120 may identify that illumination measured by the illumination sensor 240K included in the electronic device 101 meets a predetermined condition. For example, the illumination sensor 240K may receive light of the environment 410. The illumination sensor 240K may provide information on the light of the environment 410 to the processor 120. The processor 120 may determine illumination of the environment 410 on the basis of the provided information on the light. The processor 120 may compare the determined illumination with predetermined illumination. The predetermined illumination may be used to determine whether a brightness of a lighting device located within the environment 410 is changed for sleep. The predetermined illumination may be adaptively changed according to an environment. The processor 120 may identify that the determined illumination is smaller than the predetermined illumination on the basis of the comparison result. The processor 120 may identify that the illumination meets the predetermined condition on the basis of the identification that the determined illumination is smaller than the predetermined illumination. Operation 910 may be omitted according to embodiments.

In operation 920, the processor 120 may transmit the RF signal through the RF sensor 240N. The processor 120 may change the operation state of the RF sensor 240N from an inactive state (or an idle state) to an active state in response to the identification that the illumination meets the predetermined condition. According to some embodiments, the processor 120 may perform control to transmit the RF signal through the RF sensor 240N according to a predetermined period. According to other embodiments, the processor 120 may perform control to continuously transmit the RF signal through the RF sensor 240N. The processor 120 may save power consumed by the RF sensor 240N by activating the RF sensor 240N on the basis of the condition indicating whether the illumination meets the predetermined condition.

In operation 930, the processor 120 may control the RF sensor 240N to receive a reflection signal of the RF signal. The reflection signal may be received through one or more antennas included in the RF sensor 240N.

In operation 940, the processor 120 may monitor the received reflection signal. The processor 120 may monitor the reflection signal in order to identify a change in the reflection signal. The processor 120 may monitor the received reflection signal in order to determine whether the user or the object is located within the designated area 420. For example, the processor 120 may compare the received reflection signal with the RF signal. In this case, the RF signal may be used as a reference signal for determining the degree or size of the change in the reflection signal. The processor 120 may monitor whether a difference between the reflection signal and the RF signal is out of a predetermined range. In another example, the processor 120 may compare a currently received reflection signal with a reflection signal received before a specific time interval from now. The processor 120 may monitor whether a difference between the previously received reflection signal and the currently received reflection signal is out of a predetermined range.

In operation 950, the processor 120 may determine that the user or the object is located within the designated area 420 in response to monitoring that the change in the reflection signal is output of the predetermined range. A characteristic or attribute of the reflection signal received by the electronic device 101 in the state in which the user enters the designated area 420 may be different form a characteristic or attribute of the reflection signal received by the electronic device 101 in the state in which the user does not enter the designated area 420. The processor 120 may determine whether the user or the object is located within the designated area 420 by monitoring that the change in the reflection signal is out of the predetermined range.

In operation 960, the processor 120 may identify one or more signals within the reflection signal through one or more filters within the RF Sensor 240N in response to the determination that the user is located within the designated area. For example, the processor 120 may transmit control information for activating one or more filters within the RF sensor 240N to the RF sensor 240N in response to the determination that the user is located within the designated area. The RF sensor 240N may receive the control information. The RF sensor 240N may activate the one or more filters on the basis of the control information. The one or more filters may extract one or more signals indicating the state of the user from the reflection signal. For example, a first filter included in the one or more filters may extract a first signal in a first band by filtering (or blocking) the remaining signals other than the first signal in the first band within the reflection signal. The extracted first signal may be a signal indicating the motion state of the user. In another example, a second filter included in the one or more filters may extract a second signal in a second band by filtering the remaining signals other than the second signal in the second band within the reflection signal. The extracted second signal may be a signal indicating the breath state of the user. In another example, a third filter included in the one or more filters may extract a third signal in a third band by filtering the remaining signals other than the third signal in the third band within the reflection signal.

Figure 10:
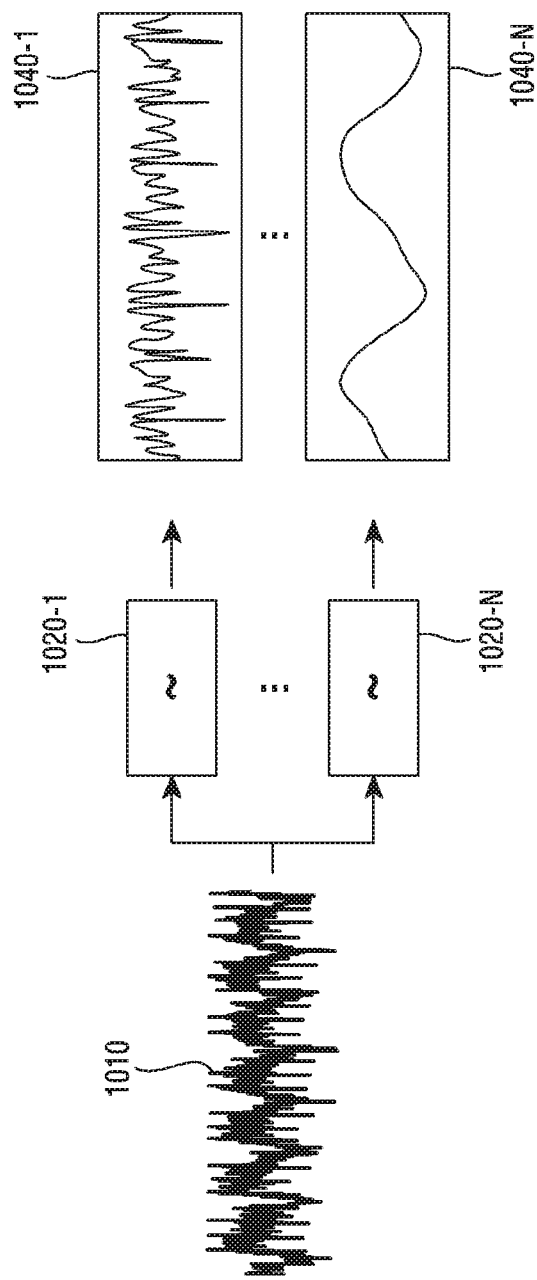
FIG. 10 illustrates an example of one or more signals identified within a reflection signal according to various embodiments.

For example, referring to FIG. 10, the RF Sensor 240N may receive a reflection signal 1010. The reflection signal 1010 may include a plurality of signals related to a plurality of bands. The reflection signal 1010 may be filtered by one or more filters 1020-1 to 1020-N within the RF sensor 240N activated on the basis of the control of the processor 120. For example, the filter 1020-1 may allow a signal 1040-1 in the first band within the reflection signal 1010 to pass therethrough. The processor 120 may receive information on the signal 1040-1 having passed through the filter 1020-1. In another example, the filter 1020-N may allow a signal 1040-N in the second band lower than the first band within the reflection signal 1010 to pass therethrough. The processor 120 may receive information on the signal 1040-N having passed through the filter 1020-N.

The processor 120 may save power consumed due to the operation of the one or more filters by activating the one or more filters included in the RF sensor 240N on the basis of the condition indicating that the user is located within the designated area. The one or more filters included in the RF sensor 240N are activated on the basis of the condition indicating that the user is located within the designated area in operation 960 of FIG. 9, but it should be noted that the one or more filters may operate in the active state regardless of the condition according to embodiments.

In operation 970, the processor 120 may store data determined on the basis of the reflection signal in response to the determination that the user is located within the designated area. According to some embodiments, the data may include information on the reflection signal. According to other embodiments, the data may include information on the one or more identified signals within the reflection signal. According to other embodiments, the data may include information on a feature value or a processed value indicating the state of the user determined on the basis of the one or more signals. According to other embodiments, the data may include information on a probability of the sleep state of the user determined on the basis of the feature value or the processed value. In other words, the processor 120 may directly store the information on the reflection signal without processing or store a value obtained by processing the information on the reflection signal (for example, a feature value or a probability value obtained on the basis of the reflection signal).

The processor 120 may secure a storage capacity of the memory 130 included in the electronic device 101 by storing the data on the basis of the condition indicating that the user is located within the designated area. The data is stored on the basis of the condition indicating that the user is located within the designated area in operation 970 of FIG. 7, but it should be noted that the data may be stored regardless of the condition according to embodiments.

Figure 11:
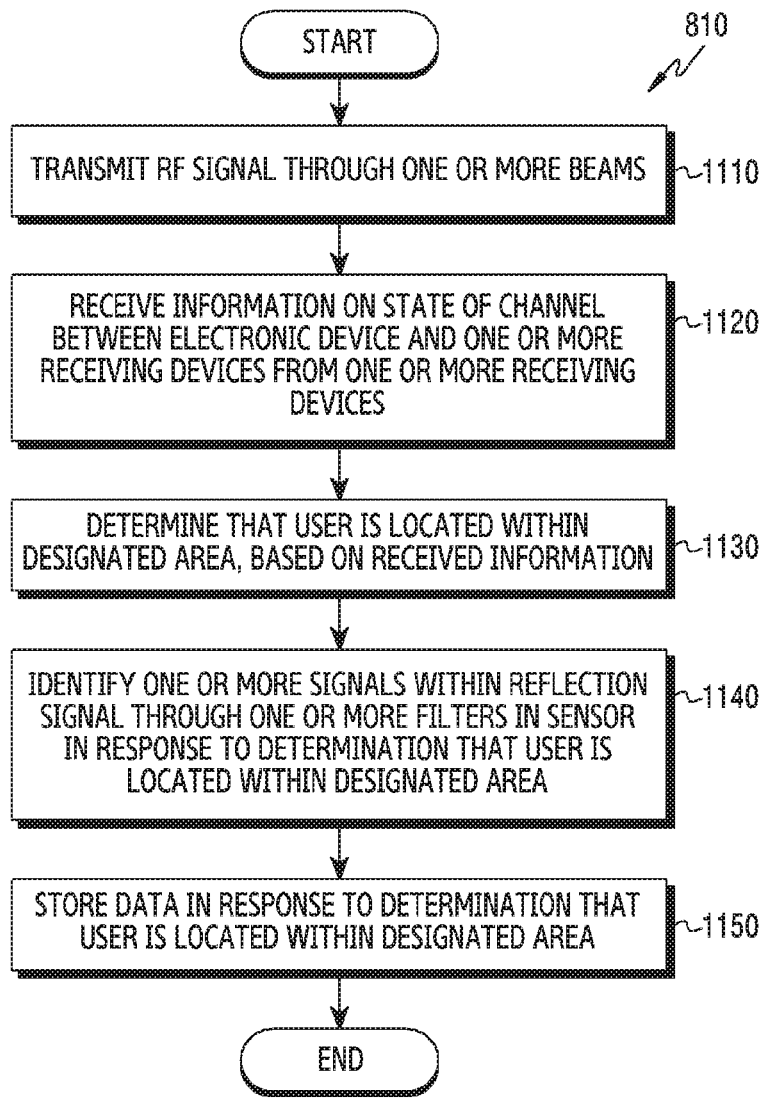
FIG. 11 illustrates an example of the operation of the electronic device for transmitting an RF signal through one or more beams according to various embodiments.

FIG. 11 illustrates an example of the operation of the electronic device for transmitting an RF signal through one or more beams according to various embodiments. The operation may be performed by the electronic device 101 illustrated in FIG. 1 or an element (for example, the processor 120) included in the electronic device 101.

In FIG. 11, operations 1110 to 1150 may be related to operation 810 of FIG. 8.

Figure 12:
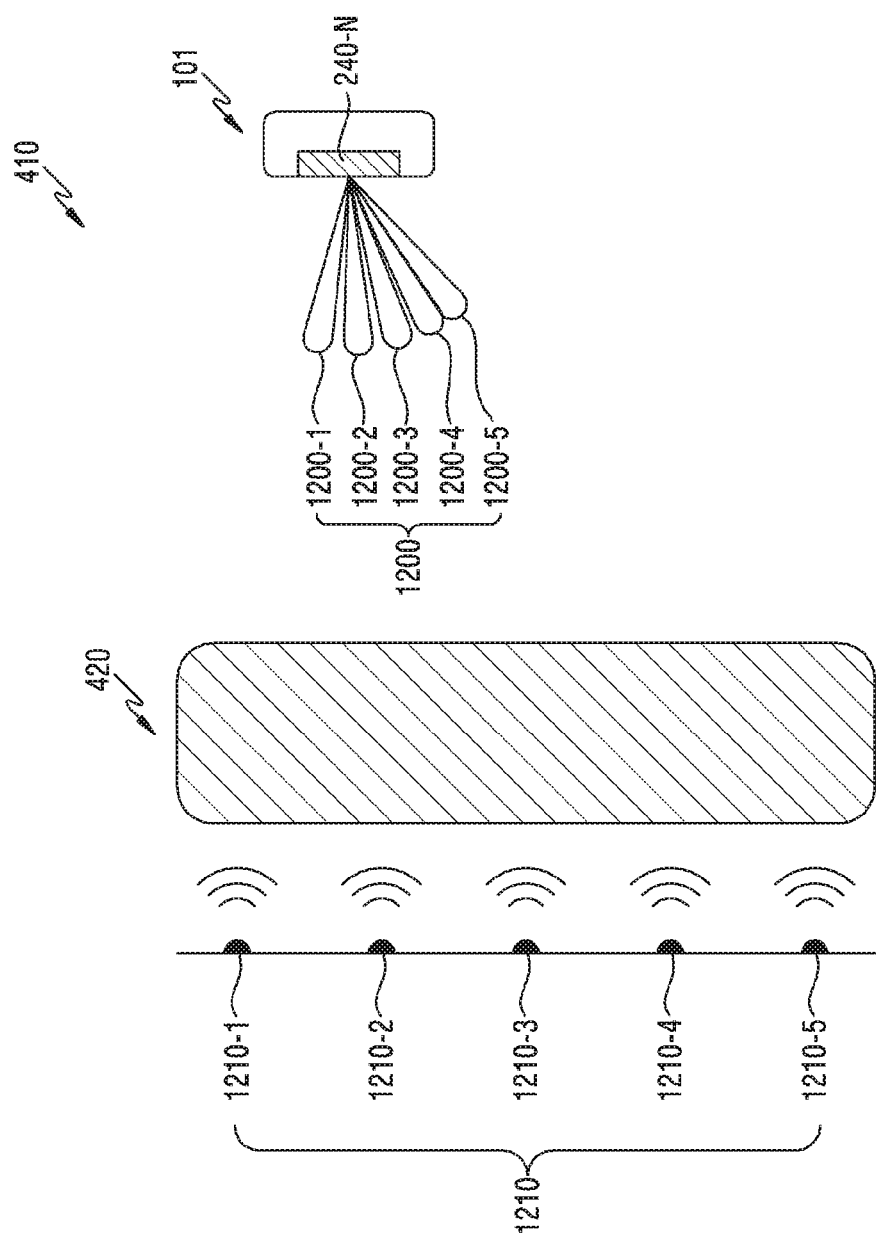
FIG. 12 illustrates an example of an environment including the electronic device for transmitting an RF signal through one or more beams according to various embodiments.

Referring to FIG. 11, in operation 1110, the processor 120 may control the RF sensor 240N to transmit the RF signal through one or more beams. The one or more beams may be configured in directions from the electronic device 101 to one or more receiving devices or receiving ends disposed or installed within the environment 410. Referring to FIG. 12, the environment 410 may further include one or more receiving devices 1210. Each of the one or more receiving devices 1210 may be used to feedback (or provide) information on the state of a channel between the electronic device 101 and each of the one or more receiving devices 1210, related to the one or more beams, to the electronic device 101. Each of the one or more receiving devices 1210 may be used to feedback (or provide) information on a quality of the RF signal transmitted by the electronic device 101 through the one or more beams to the electronic device 101. The one or more receiving devices 1210 may be disposed on the opposite side of the electronic device 101 in order to identify whether the user is located within the designated area 420. For example, the electronic device 101 may be disposed on one side of the designated area 420, and the one or more receiving devices 1210 may be disposed on the other side of the designated area 420. A first beam 1200-1 of the one or more beams may be configured in a direction from the electronic device 101 to a receiving device 1210-1. A second beam 1200-2 of the one or more beams may be configured in a direction from the electronic device 101 to a receiving device 1210-2. A third beam 1200-3 of the one or more beams 1200 may be configured in a direction from the electronic device 101 to a receiving device 1210-3. A fourth beam 1200-4 of the one or more beams may be configured in a direction from the electronic device 101 to a receiving device 1210-4. A fifth beam 1200-5 of the one or more beams may be configured in a direction from the electronic device 101 to a receiving device 1210-5. The processor 120 may transmit the RF signal through each of the one or more beams 1200 directing to each of the one or more receiving devices 1210 through the RF sensor 240-N. According to some embodiments, the RF signal transmitted through each of the one or more beams 1200 may include information on transmission power of the RF signal. The information on the transmission power of the RF signal may be used to determine a reception gain of the RF signal.

In operation 1120, the processor 120 may control the RF sensor 240N to receive information on the state of a channel between the electronic device 101 and each of the one or more receiving devices from the one or more receiving devices. For example, referring to FIG. 12, the processor 120 may receive the information on the state of the channel between the electronic device 101 and each of the one or more receiving devices 1210 from each of the one or more receiving devices 1210. The information on the state of the channel may include information related to the reception gain or reception quality of the RF signal. For example, the information on the state of the channel may include one or more of a Channel State Indication (CSI), a Channel Quality Indication (CQI), a Received Signal Strength Indication (RSSI), or a Signal to Noise Ratio (SNR). According to some embodiments, the information on the state of the channel may include information on a difference between a reception gain (or strength) of the RF signal transmitted in a first period and a reception gain of the RF signal transmitted in a second period that is the subsequent period of the first period. According to other embodiments, the information on the state of the channel may include information on a difference between a transmission strength of the RF signal and a reception strength of the RF signal. For example, the processor 120 may receive information on the state of the channel related to the first beam 1200-1 from the receiving device 1210-1, information on the state of the channel related to the second beam 1200-2 from the receiving device 1210-2, information on the state of the channel related to the third beam 1200-3 from the receiving device 1210-3, information on the state of the channel related to the fourth beam 1200-4 from the receiving device 1210-4, and information on the state of the channel related to the fifth beam 1200-5 from the receiving device 1210-5.

When the user is located within the designated area 420, the state of the channel (or the reception gain of the RF signal) related to at least some of the one or more beams 1200 may be lower than the state of the channel related to at least some of the one or more beams 1200 in the case in which the user is not located within the designated area 420. This is because the user located within the designated area 420 may act as interference of the RF signal. The processor 120 may transmit the RF signals through the one or more beams 1200 and receive feedbacks related to the RF signals from the one or more receiving devices, so as to determine whether the user is located within the designated area 420.

In operation 1130, the processor 120 may determine that the user is located within the designated area on the basis of the received information on the state of the channel. For example, when it is identified that the state of at least some of the one or more channels related to the one or more beams 1200 is rapidly changed, the processor 120 may determine that the user is located within (or enters) the designated area 420. In another example, when it is identified that the state of the one or more channels related to the one or more beams 1200 is not changed, the processor 120 may determine that the user is not located within (or does not enter) the designated area 420.

Operations 1140 and 1150 may correspond to operations 960 and 970 of FIG. 9, respectively.

The environment 410 in which the electronic device 101 is located does not include one or more receiving devices 1210 for performing the feedback on the RF signal. In this case, the processor 120 may determine that the user is located in the designated area 420 by analyzing a reflection signal of the transmitted RF signal. The processor 120 may estimate the location of the user (or a specific object) within the designated area 420 on the basis of the determination. The processor 120 may control one or more directivity antennas included in the electronic device 101 to form beams in a direction corresponding to the estimated located of the user. The processor 120 may perform control to transmit the RF signals through the beams formed using the one or more directivity antennas. The processor 120 may determine the state related to the sleep of the user located within the designated area 420 on the basis of reception of the reflection signal of the RF signal transmitted through the beam.

As described above, the processor 120 of the electronic device 101 according to various embodiments may determine whether the user is located within the designated area 420 by transmitting the RF signals through one or more beams in an ultra high frequency band. Since the RF signal transmitted in the ultra high frequency band is sensitive to interference due to high straightness thereof, the processor 120 may monitor whether the state of the designated area 420 related to the user or the object is changed through the feedback of the RF signal. In other words, the electronic device 101 according to various embodiments may determine whether the user is located within the designated (or specific) area 420 which is a space to measure the sleep state of the user without any user input or intervention of the user.

Figure 13:
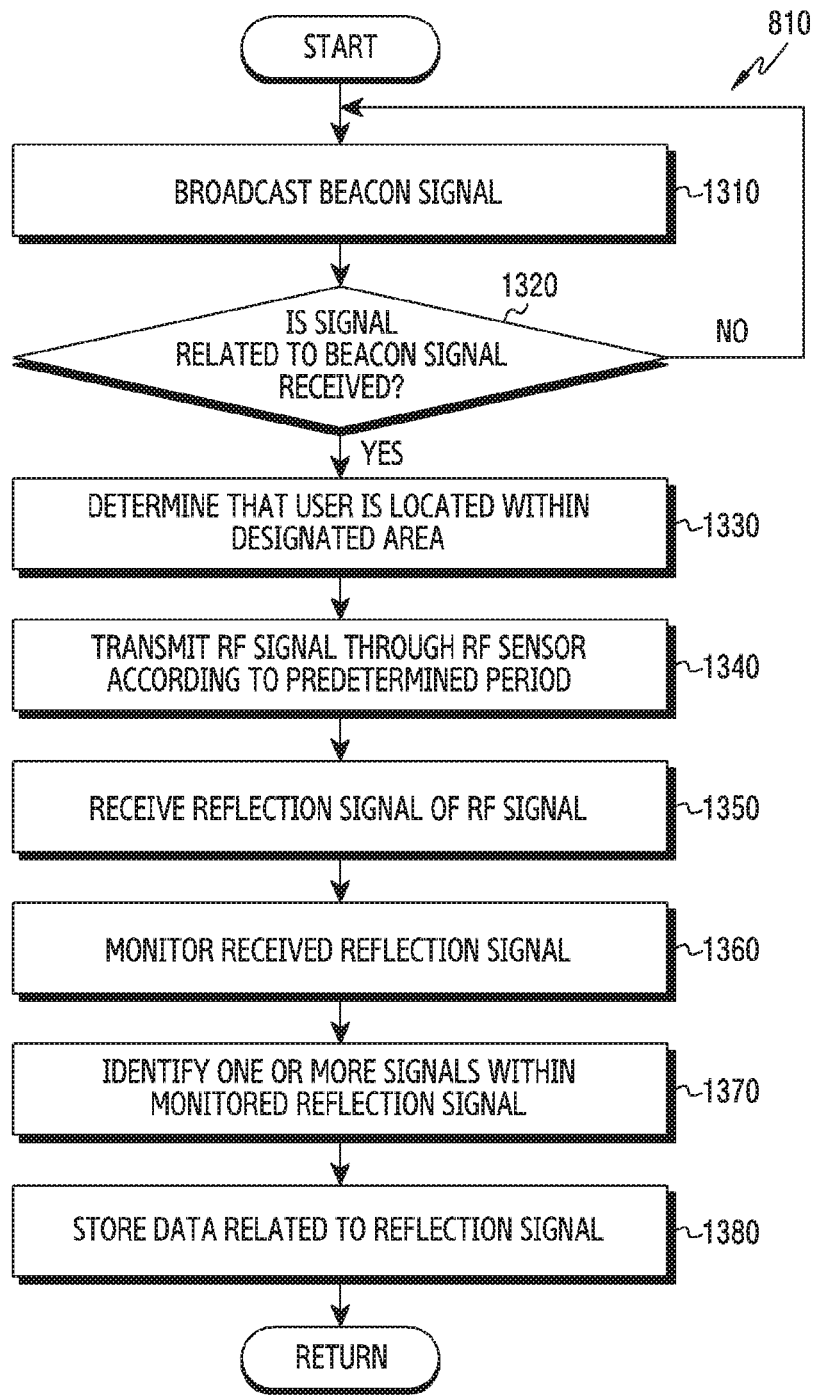
FIG. 13 illustrates an example of the operation of the electronic device for identifying whether the user is located within the designated area through a beacon signal according to various embodiments.

FIG. 13 illustrates an example of the operation of the electronic device for identifying whether the user is located within the designated area through a beacon signal according to various embodiments. The operation may be performed by the electronic device 101 illustrated in FIG. 1 or an element (for example, the processor 120) within the electronic device 101.

In FIG. 13, operations 1310 to 1380 may be related to operation 810 of FIG. 8.

Figure 14:
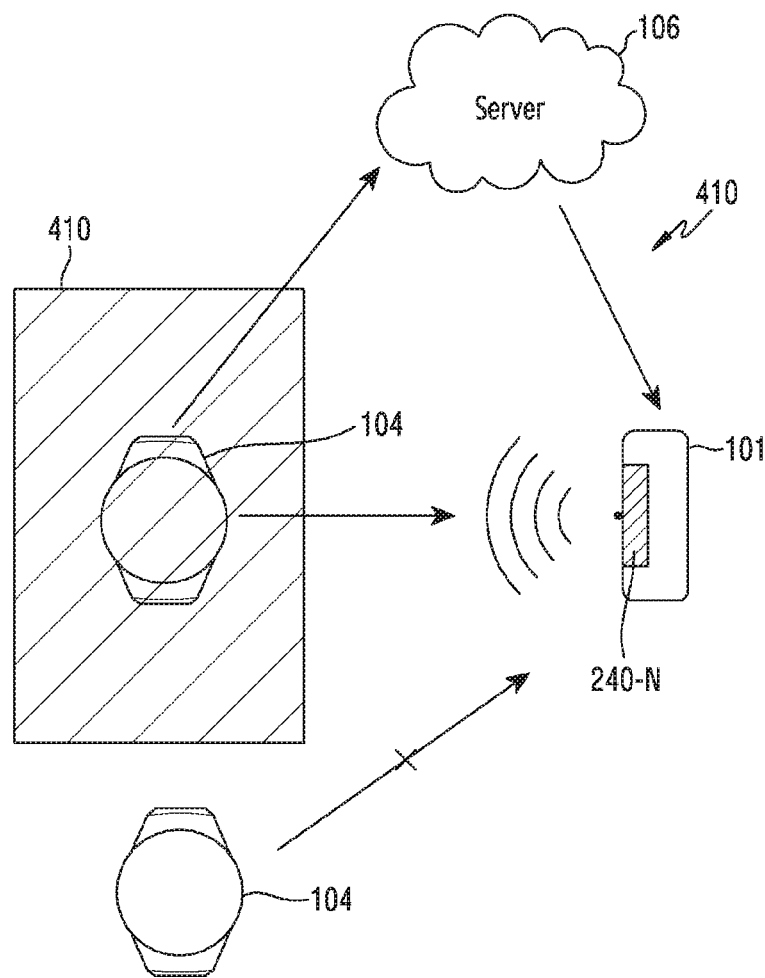
FIG. 14 illustrates an example of an environment including the electronic device for identifying whether the user is located within a designated area through a beacon signal according to various embodiments.

Referring to FIG. 13, in operation 1310, the processor 120 may control the communication module 220 to broadcast a beacon signal. For example, the processor 120 may control the BT module 225 within the communication module 220 to broadcast the beacon signal. The beacon signal may be used to determine whether the user is located within the designated area 420. The beacon signal may include an identifier or an identification (ID) indicating the electronic device 101. The ID may be a medium access control (MAC) address or a MAC ID of the electronic device 101. Referring to FIG. 14, the processor 120 may broadcast the beacon signal through the communication module 220 of the electronic device 101 disposed within the environment 410. The beacon signal may be broadcasted to the designated area 420. For example, the area in which the beacon signal can be received may correspond to the designated area 420. In other words, the coverage area of the beacon signal may correspond to the designated area 420. For example, another electronic device 104 located outside the designated area 420 may not receive the beacon signal. In another example, another electronic device 104 located within the designated area 420 may receive the beacon signal.

In operation 1320, the processor 120 may monitor whether a signal related to the transmitted beacon signal is received. The processor 120 may monitor whether the signal related to the transmitted beacon signal is received in order to identify whether another electronic device 104 is located within (or enter) the designated area 420. Another electronic device 104 may be a wearable device (for example, a smart watch) which the user can wear. Another electronic device 104 may have a capability to receive the beacon signal. The processor 120 may monitor whether the signal related to the beacon signal is received in order to identify whether the user wearing another electronic device 104 is located within the designated area 240.

Another electronic device 104 may transmit the signal related to the beacon signal in response to reception of the beacon signal. Referring to FIG. 14, according to some embodiments, another electronic device 104 may transmit the signal related to the beacon signal to the electronic device 101 through a communication path (for example, a Bluetooth communication path) between the electronic device 101 and another electronic device 104. The signal related to the beacon signal may indicate that another electronic device 104 is located within the designated area 420. The electronic device 101 may receive the signal related to the beacon signal. According to other embodiments, another electronic device 104 may transmit the signal related to the beacon signal to the server 106 linked to another electronic device 104. When the signal related to the beacon signal is transmitted to the server 106, the signal related to the bacon signal may include information on an identifier of the electronic device 101 and information on an identifier of another electronic device 104 (for example, a MAC ID of another electronic device 104 or a MAC address of another electronic device 104). The server 106 may transmit a signal indicating that another electronic device 104 receives the beacon signal to the electronic device 101 on the basis of reception of the signal related to the beacon signal including the information on the identifier of the electronic device 101 and the information on the identifier of another electronic device 104. The electronic device 101 may receive the signal indicating that another electronic device 104 receives the beacon signal.

When the signal related to the beacon signal (or the signal indicating that another electronic device 104 receives the beacon signal) is received, the processor 120 may perform operation 1330. Unlike this, when the signal related to the beacon signal is not received, the processor 120 may repeatedly perform operation 1310 and operation 1320.

In operation 1330, the processor 120 may determine that the user is located within the designated area in response to reception of the signal related to the beacon signal. Since the coverage area of the beacon signal corresponds to the designated area 420, reception of the signal related to the beacon signal may indicate that the user wearing another electronic device 104 is located within the designated area 420. The processor 120 may estimate or determine that the user is located within the designated area on the basis of the signal received from another electronic device 104 (or the server 106).

In operation 1340, the processor 120 may transmit the RF signal through the RF sensor 240N. For example, the processor 120 may switch the inactive state of the RF sensor 240N to the active state in response to the determination that the user is located within the designated area. The processor 120 may reduce power consumption required for the operation of the RF sensor 240N by activating the RF sensor 240N on the basis of the condition indicating that the user is located within the designated area. The processor 120 may transmit the RF signal through the activated RF sensor 240N in response to the determination that the user is located within the designated area.

Operation 1350 and operation 1360 may correspond to operation 930 and operation 940 illustrated in FIG. 9, respectively.

In operation 1370, the processor 120 may identify one or more signals within the monitored reflection signal. For example, the processor 120 may identify one or more signals within the reflection signal as illustrated in FIG. 10.

In operation 1380, the processor 120 may store data related to the received reflection signal. For example, the processor 120 may store data related to the reflection signal as shown in operation 970.

As described above, the processor 120 of the electronic device 101 according to various embodiments may determine whether the user is located within the designated area 420 through a beacon signal distinguished from the RF signal. Since power required for transmitting the beacon signal may be smaller than power required for transmitting the RF signal, the processor 120 may save power required for determining whether the user is located within the designated area 420 through the operation illustrated in FIG. 13.

Figure 15:
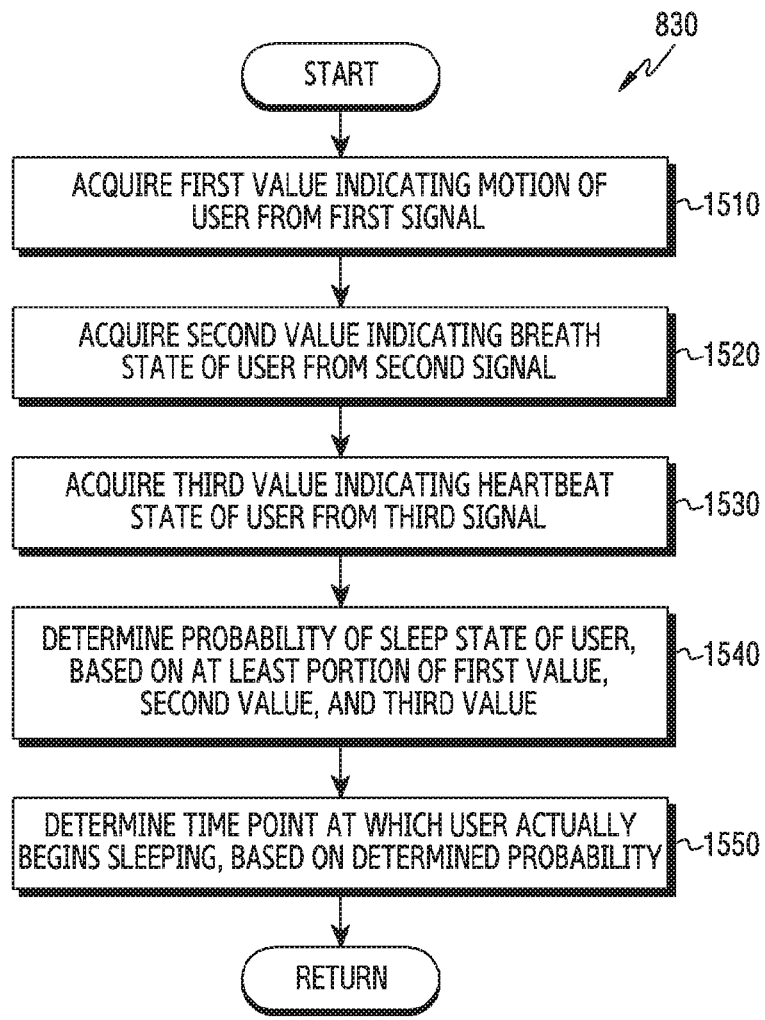
FIG. 15 illustrates an example of the operation of the electronic device for acquiring values indicating the state of the user from one or more signals according to various embodiments.

FIG. 15 illustrates an example of the operation of the electronic device for acquiring values indicating the state of the user from one or more signals according to various embodiments. The operation may be performed by the electronic device 101 illustrated in FIG. 1 or an element (for example, the processor 120) included in the electronic device 101.

In FIG. 15, operation 1510 to operation 1550 may be included in operation 830 of FIG. 8.

Figure 16:
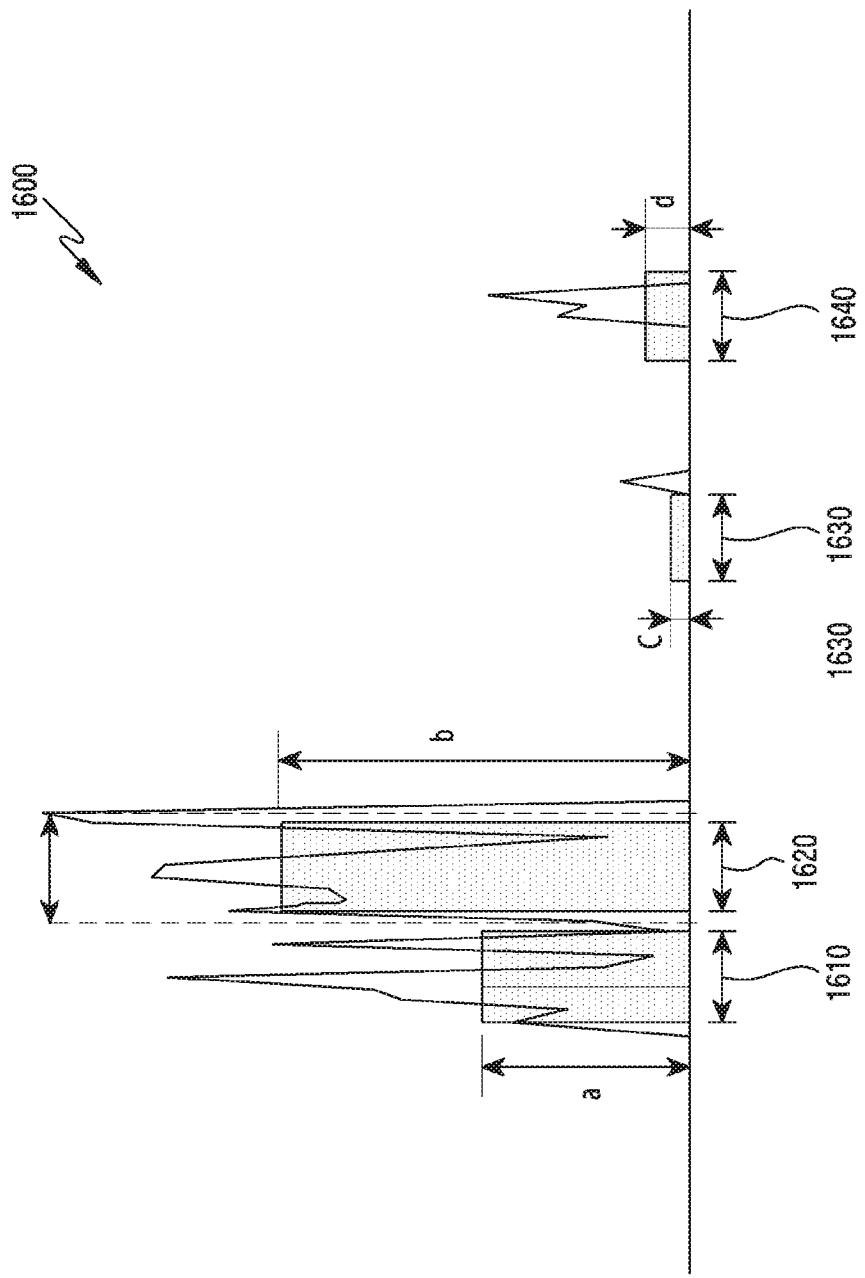
FIG. 16 is a graph illustrating a motion state of the user.
Figure 17:
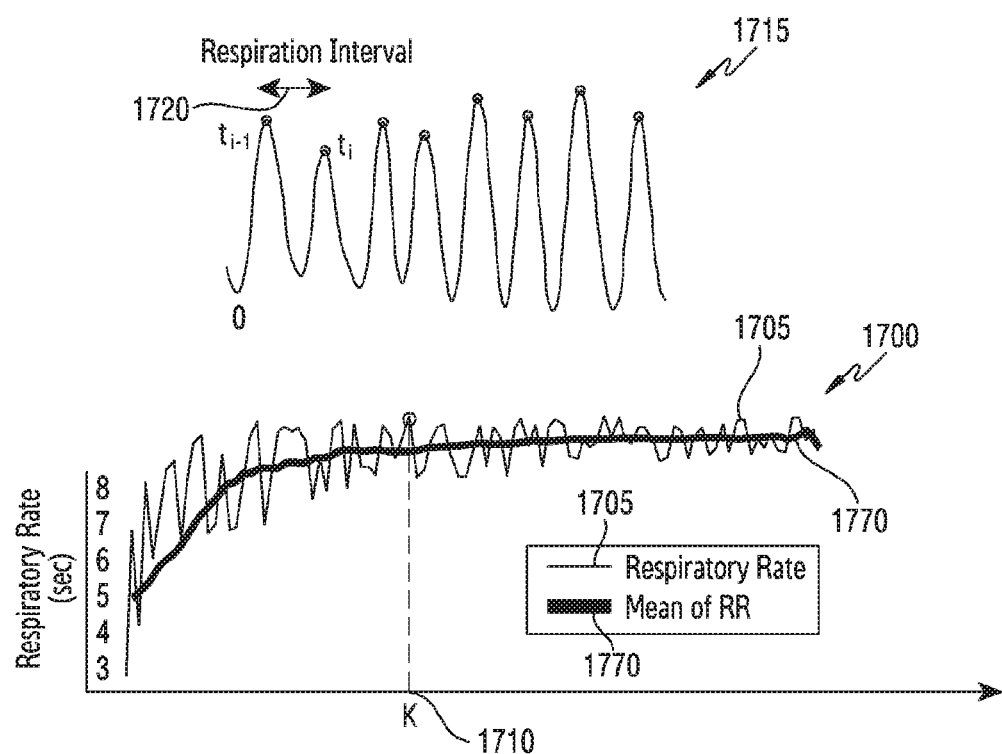
FIG. 17 is a graph illustrating a breath state of the user.
Figure 18:
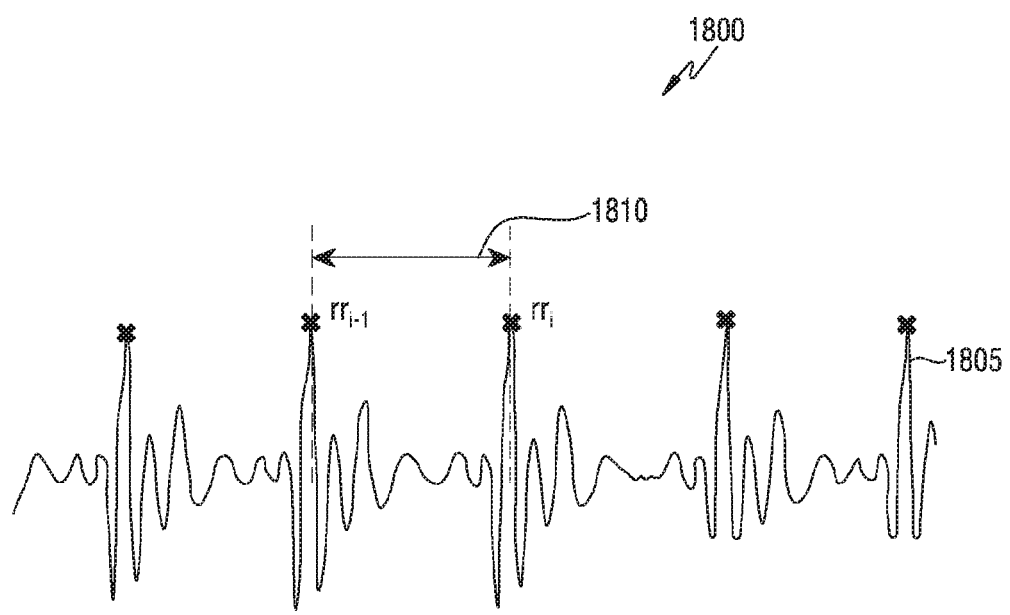
FIG. 18 is a graph illustrating a heartbeat state of the user.

Referring to FIG. 15, in operation 1510, the processor 120 may acquire or determine one or more first values indicating the motion of the user from a first signal among one or more signals identified from the reflection signal. For example, referring to FIG. 16, a graph 1600 may indicate at least a portion of the first signal. A horizontal axis of the graph 1600 may indicate a time and a vertical axis of the graph 1600 may indicate the size (for example, a degree of the motion of the user) of values (or data) included in the first signal. The processor 120 may split the first signal into specific intervals or epochs as illustrated in FIG. 16. For example, in the graph 1600, the processor 120 may split the first signal into a time interval 1610, a time interval 1620, a time interval 1630, and a time interval 1640. In other words, the processor 120 may split the first signal into a plurality of time intervals and process data of the first signal included in each of the plurality of split time intervals. For example, the processor 120 may process the data of the first signal included in each of the plurality of time intervals on the basis of Equation (1) below.

$$\text{mov}(k) = a_1 \times \text{mean}(m_k) + a_2 \times \text{median}(m_k) \qquad \text{Equation (1)}$$

In Equation (1), k denotes a kth timer interval among a plurality of timer intervals, mov(k) denotes a first value (a processed value or a feature value) indicating motion of the user in the kth time interval, mean(mk) denotes an average value of data of the first signal in the kth time interval, median(mk) denotes a median of data of the first signal in the kth interval, a1 denotes a weighted value for mean(mk), and a2 denotes a weighted value for median(mk). The processor 120 may determine first values indicating motion of the user in the plurality of time intervals on the basis of Equation (1) above. According to some embodiments, the weighted values a1 and a2 may be determined through an experiment or learning. For example, an external electronic device (for example, the server 106) other than the electronic device 101 may determine the weighted values a1 and a2 on the basis of statistical data. In another example, the electronic device 101 may determine the weighted values a1 and a2 by analyzing reliability of the first value indicating the motion of the user determined by the electronic device 101. Through the calculation operation, the processor 120 may determine that the size of mov(k) in the time interval 1610 is a, the size of mov(k) in the time interval 1620 is b larger than a, the size of mov(k) in the time interval 1630 is c smaller than a and b, and the size of mov(k) in the time interval 1640 is d smaller than a and b and larger than c. The processor 120 may identify that the motion state of the user is changed from the active state (or unstable state) to the inactive state (or stable state) by identifying that c and d are smaller than a and b.

In operation 1520, the processor 120 may acquire or determine one or more second values indicating the breath state of the user from a second signal among one or more signals identified from the reflection signal. For example, referring to FIG. 17, a graph 1700 may indicate at least a portion of the second signal. A horizontal axis of the graph 1700 may indicate a time and a vertical axis of the graph 1700 may indicate a length of a respiratory rate of the user corresponding to data included in at least a portion of the second signal. A curved line 1705 in the graph 1700 may indicate a change in the respiratory rate of the user according to the time corresponding to data included in at least a portion of the second signal, and a curved line 1770 in the graph 1700 may indicate a change in the average of the respiratory rate of the user according to the time corresponding to processed data of data included in at least a portion of the second signal. The processor 120 may split the second signal into a plurality of time intervals. For example, on the curved line 1705 of the graph 1700, the processor 120 may split the second signal into n time intervals. The respiratory rate of the user during a kth time interval among the n time intervals may be indicated by a curved line 1715. The processor 120 may identify a plurality of peak values among a plurality of values (or data) on the curved line 1715. The plurality of peak values may indicate maximum values on which the respiratory rate changes from the increase to decrease. The processor 120 may calculate an interval between the plurality of identified peak values. For example, the processor 120 may determine an interval 1720 between a time point ti−1 corresponding to a first peak value and a time point ti corresponding to a second peak value. The processor 120 may calculate each of the intervals such as the interval 1720 on the basis of the plurality of peak values. The processor 120 may determine that the average of respiratory rates of the user in the kth time interval is the second value on the basis of the calculated intervals. For example, the processor 120 may determine that the average of the respiratory rates of the user is the second value on the basis of Equation (2) below.

$$RR(k) = \sum_{i=1}^{n} \frac{t_i - t_{i-1}}{n} \quad \text{Equation (2)}$$

In Equation (2), k denotes a kth time interval among N time intervals, RR(k) denotes the average of respiratory rates of the user in the kth time interval, n denotes the number of a plurality of peak values within the kth time interval, ti denotes a time point corresponding to an ith peak value among the n peak values, and ti-1 denotes a time point corresponding to an i-1th peak value among the n peak values. The processor 120 may determine that the average of respiratory rates of the user in the kth time interval is the second value on the basis of Equation (2). The processor 120 may repeatedly perform the operation in the n time intervals. For example, the processor 120 may determine one or more second values by processing data on the second signal as indicated by the curved line 1770 of the graph 1700. The processor 120 may identify that the respiratory rate of the user is longer and constant as the time lapses through data processing as indicated by the curved line 1770.

In operation 1530, the processor 120 may acquire or determine one or more third values indicating the heartbeat state of the user from a third signal among one or more signals identified from the reflection signal. For example, referring to FIG. 18, a graph 1800 may indicate at least a portion of the third signal. A horizontal axis of the graph 1800 may indicate a time and a vertical axis of the graph 1800 may indicate a heart rate. A curved line 1805 of the graph 1800 may indicate a change in the heartbeat state of the user according to the time. The processor 120 may split the third signal into a plurality of time intervals. The processor 120 may identify a plurality of peak values in a portion of the third signal in each of the plurality of time intervals. Each of the plurality of peak values may indicates a value having the size larger than or equal to a threshold value among a plurality of values included in a portion of the third signal. Each of the plurality of peak values may indicate a normal heartbeat. The processor 120 may calculate an interval between the plurality of identified peak values. For example, the processor 120 may determine an interval 1810 between a time point rri-1 corresponding to a first peak value and a time point rri corresponding to a second peak value. The processor 120 may calculate each of the intervals such as the interval 1810 on the basis of the plurality of peak values. The processor 120 may determine that the average of heart rates of the user in a kth time interval among the plurality of time intervals is a third value on the basis of the calculated intervals. For example, the processor 120 may determine that the average of the heart rates of the user is the third value on the basis of Equation (3) below.

$$HR(k) = \sum_{i=1}^{n} \frac{rr_i - rr_{i-1}}{n} \quad \text{Equation (3)}$$

In Equation (3), k denotes a kth time interval among a plurality of time intervals, HR(k) denotes the average of heart rates of the user in the kth time interval, rri denotes a time point corresponding to an ith peak value among the n peak values, and rri-1 denotes a time point corresponding to i-1th peak value among the n peak values. The processor 120 may determine that the average of heart rates of the user in the kth time interval is the third value on the basis of Equation (3). The processor 120 may determine the third value in each of the plurality of time intervals by repeatedly performing the operation in the plurality of n time intervals.

In another example, the processor 120 may determine that the average of heart rates of the user is the third value through Standard Deviation of NN interval (SDNN) as shown in Equation (4).

$$SDNN = \frac{1}{n}\sqrt{\sum_{i=1}^{n}(rr_i - \overline{rr})^2} \quad \text{Equation (4)}$$

In Equation (4), SDNN denotes another example of the third value, n denotes the number of a plurality of peak values, rri denotes a time point corresponding to an ith peak value among the plurality of n peak values, and $\overline{rr}$ denotes the average of intervals between the n peak values.

In another example, the processor 120 may determine that the average of heart rates of the user is the third value through Root Mean Square of Successive Difference (RMSSD) as shown in Equation (5).

$$RMSSD = \frac{1}{n}\sqrt{\sum_{i=1}^{n}(rr_i - rr_{i+1})^2} \quad \text{Equation (5)}$$

In Equation (5), RMSSD denotes another example of the third value, n denotes the number of a plurality of peak values, rri denotes a time point corresponding to an ith peak value among the plurality of n peak values, and rri+1 denotes a time point corresponding an i+1th peak value among the plurality of n peak values.

According to some embodiments, the processor 120 may calculate the one or more third values from the third signal through analysis of heart rate variation in a frequency domain.

FIG. 15 illustrates an example in which the processor 120 performs operation 1520 after operation 1510 and performs operation 1530 after operation 1520, but this is only for convenience of description. Operation 1510, operation 1520, and operation 1530 may be performed regardless of order or may be actually performed at the same time.

In operation 1540, the processor 120 may determine a probability of the sleep state of the user on the basis of at least some of the first value, the second value, and the third value. The processor 120 may determine the probability of the sleep state of the user by assigning a weighted value to each of the first value, the second value, and the third value. For example, the processor 120 may determine the probability of the sleep state of the user on the basis of Equation (6).

$$\text{Prob}_k = c_1 f_1(\text{mov}_k) + c_2 f_2(RR_k) + c_3 f_3(HR_k) \quad \text{Equation (6)}$$

In Equation (6), Probk denotes a probability of the sleep state of the user in a kth time interval among n time intervals, f1(movk) denotes one or more first values indicating the motion state of the user in the kth time interval, f2(RRk)

denotes one or more second values indicating the breath state of the user in the kth time interval, f3(HRk) denotes one or more third values indicating the breath state of the user in the kth time interval, c1 denotes a weighted value for the one or more first values, c2 denotes a weighted value for the one or more second values, and c3 denotes a weighted value for the one or more third values. The weighted values may be determined on the basis of statistics or learning.

Figure 19:
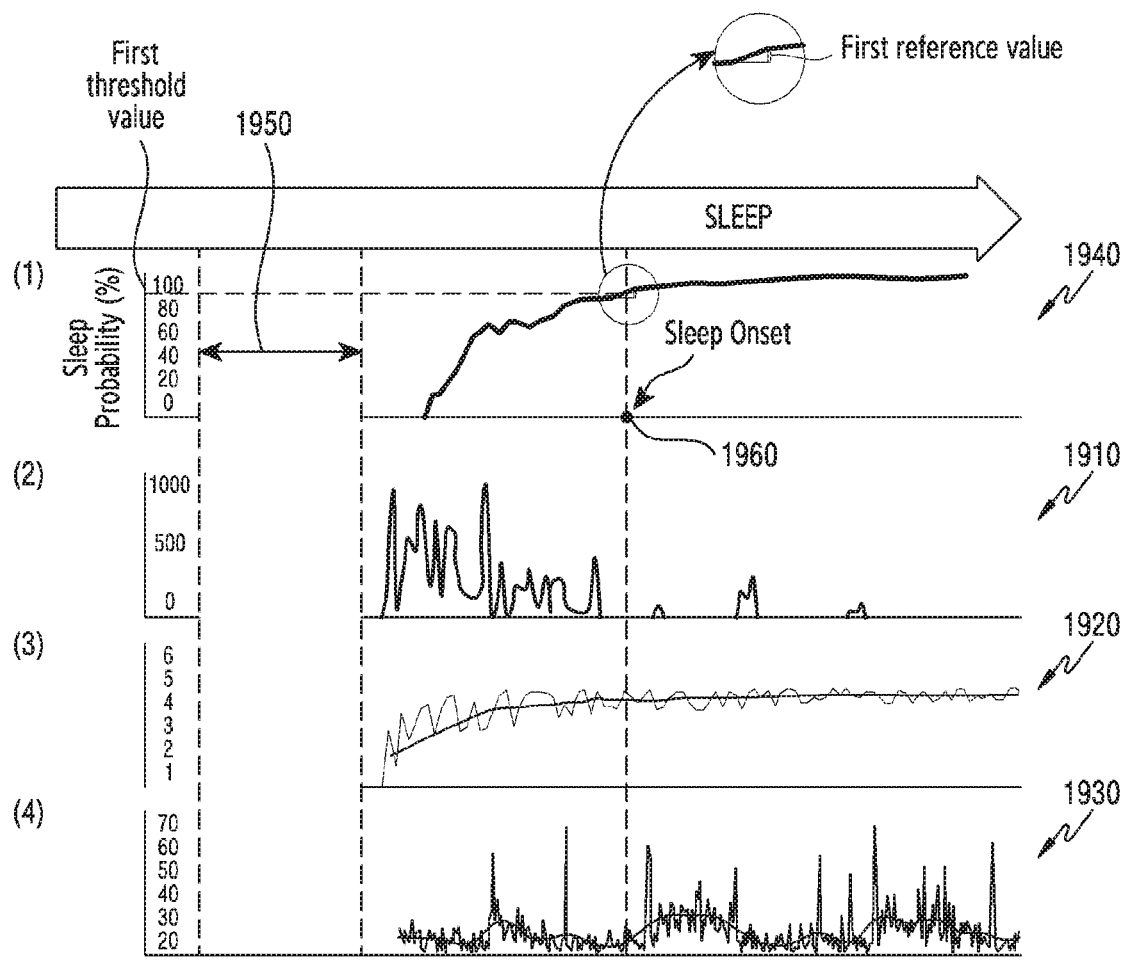
FIG. 19 is a graph illustrating a time point at which the user actually begins sleeping.

For example, referring to FIG. 19, a graph 1910 may indicate the motion state of the user, a horizontal axis of the graph 1910 may indicate a time, and a vertical axis of the graph 1910 may indicate a degree of the motion of the user. A graph 1920 may indicate the breath state of the user, a horizontal axis of the graph 1920 may indicate a time, and a vertical axis of the graph 1920 may indicate a respiratory rate of the user. A graph 1930 may indicate the heartbeat state of the user, a horizontal axis of the graph 1930 may indicate a time, and a vertical axis of the graph 1930 may indicate an average heart rate. A graph 1940 may indicate a probability of the sleep state of the user determined on the basis of data included in the graph 1910, data included in the graph 1920, and data included in the graph 1930. A horizontal axis of the graph 1940 may indicate a time and a vertical axis of the graph 1940 may indicate a probability. The graph 1910, the graph 1920, the graph 1930, and the graph 1940 may be temporally synchronized. In the graph 1910, the graph 1920, the graph 1930, and the graph 1940, an interval 1950 may indicate a time during which the user is not located within the designated area 420. The time corresponds to a time point at which no motion of the user, no breath of the user, or no heartbeat of the user is detected.

The processor 120 may determine the probability of the sleep state of the user as indicated by the graph 1940 on the basis of Equation (6).

In operation 1550, the processor 120 may determine a time point at which the user actually begins sleeping on the basis of the determined probability. For example, the processor 120 may identify that a time point at which a change in the determined probability according to the time is smaller than a first reference value is the time point at which the user actually begins sleeping. In the graph 1940, the processor 120 may identify that a time point 1960 at which the change in the determined probability according to the time is smaller than the first reference value is the time point at which the user actually begins sleeping. In another example, the processor 120 may identify that the time point 1960 at which the determined probability is larger than a first threshold value is the time at which the user actually begins sleeping. In another example, the processor 120 may identify that the time point 1960 at which the determined probability is larger than the first threshold value and the change in the determined probability according to the time is smaller than the first reference value is the time at which the user actually begins sleeping.

Operation 1510 to operation 1550 are only examples for determining the value indicating the state of the user from one or more signals within the reflection signal and determining that the determined value is the probability. The processor 120 of the electronic device 101 according to various embodiments may perform other operations without limiting to operations 1510 to 1550. According to some embodiments, the processor 120 may determine the probability of the sleep state of the user on the basis of one or more values indicating the state of the user through rule-based learning or machine learning. The processor 120 may further process information on the determined probability. For example, the processor 120 may transform the determined probability to a linear sum using one or more of a first-order differential, a second-order differential, and a higher-order differential such as a third-order differential of the probability. Further, the processor 120 may identify whether the user is in a sleep state through a classifier on the basis of a value calculated through the linear sum as an input value. For example, the processor 120 may identify whether the user is in the sleep state on the basis of a machine learning model such as Support Vector Machine (SVM), Hidden Markov Model (HMM), or Recurrent Neural Network (RNN).

As described above, the processor 120 of the electronic device 101 according to various embodiments may determine the probability of the sleep state of the user without any intervention of the user. Further, the processor 210 may determine the time point at which the user actually begins sleeping without any intervention of the user.

Figure 20:
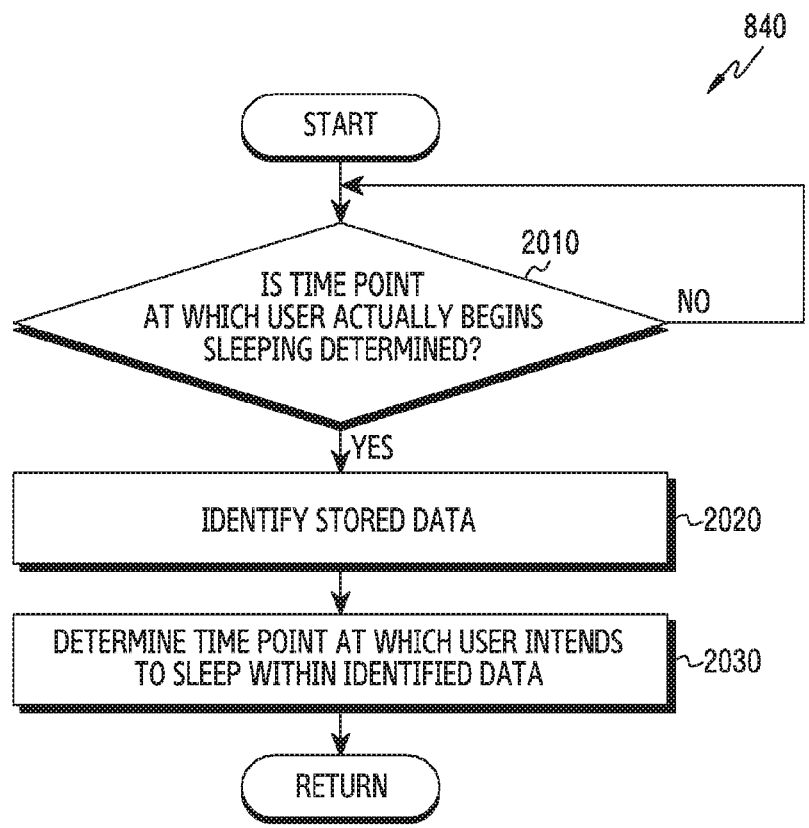
FIG. 20 illustrates an example of the operation of the electronic device for determining a time point at which the user intends to sleep according to various embodiments.

FIG. 20 illustrates an example of the operation of the electronic device for determining a time point at which the user intends to sleep according to various embodiments. The operation may be performed by the electronic device 101 illustrated in FIG. 1 or the element (for example, the processor 120) of the electronic device 101.

In FIG. 20, operations 2010 to 2030 may be related to operation 840 of FIG. 8.

Referring to FIG. 20, in operation 2010, the processor 120 may identify whether to determine the time point at which the user actually begins sleeping. For example, the processor 120 may identify whether the time point at which the user actually begins sleeping is determined in order to determine whether to trigger analysis of data related to the one or more signals and stored in the memory 130. The processor 120 may perform operation 2020 in response to the determination of the time point at which the user actually begins sleeping. Unlike this, when the processor 120 does not determine the time point at which the user actually begins sleeping, the processor 120 may repeatedly perform operation 2010.

In operation 2020, the processor 120 may identify stored data in response to the determination of the time point at which the user actually begins sleeping. For example, the processor 120 may identify stored data through operation 970 of FIG. 9, operation 1150 of FIG. 11, or operation 1380 of FIG. 13. The processor 120 may monitor the stored data in order to determine a time point at which the user intends to sleep.

Figure 21:
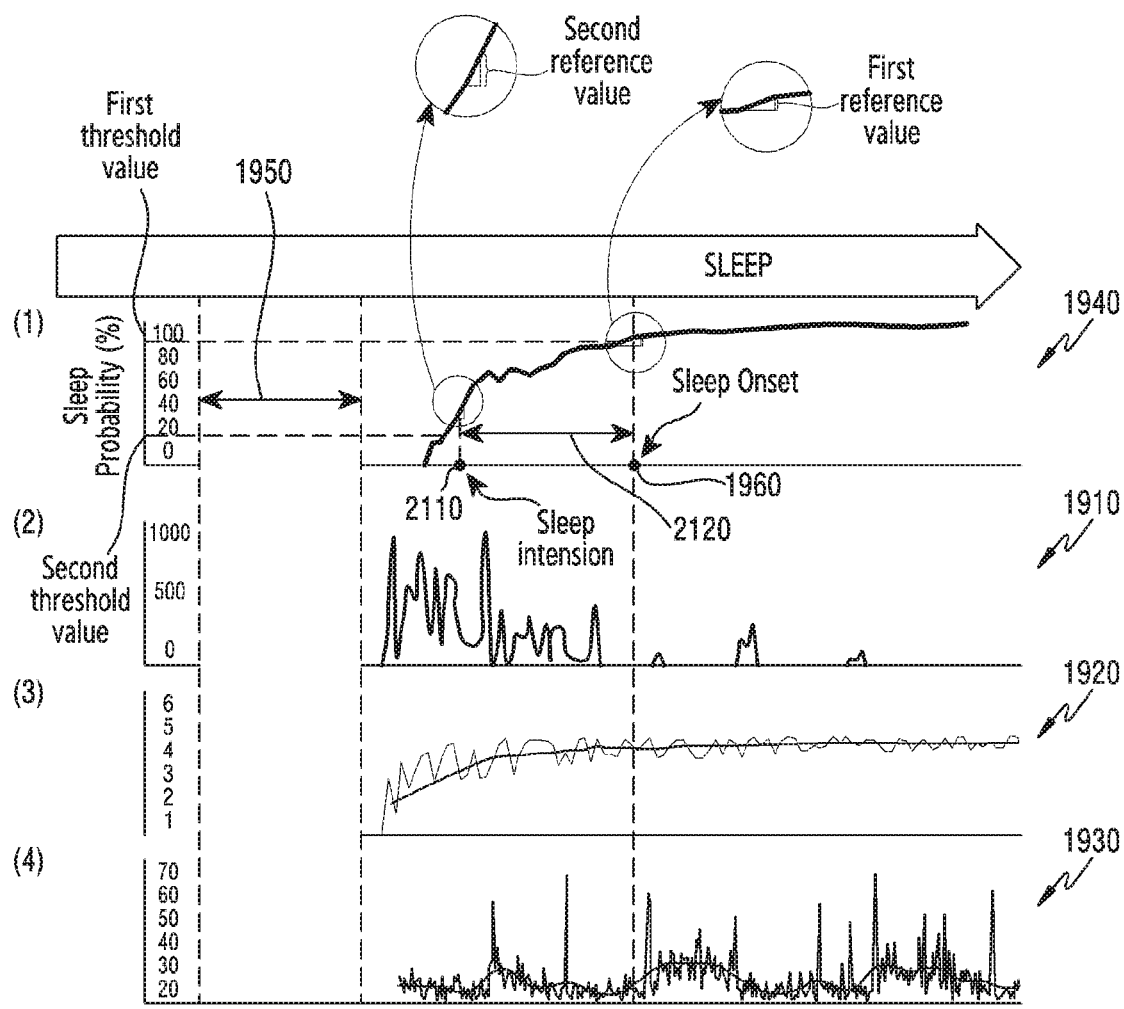
FIG. 21 is a graph illustrating a time point at which the user intends to sleep.

In operation 2030, the processor 120 may determine the time point at which the user intends to sleep within the identified data. For example the processor 120 may determine that a time point at which the probability of the sleep state of the user is larger than a second reference value is the time point at which the user intends to sleep. Referring to FIG. 21, in a graph 1940, the processor 120 may determine that a time point 2110 at which a change in the probability according to the time is larger than a second reference value is the time point at which the user intends to sleep. In another example, the processor 120 may determine that the time point 2110 at which the determined probability is larger than a second threshold value is the time point at which the user intends to sleep. In another example, the processor 120 may determine that the time point 2110 at which the determined probability is larger than the second threshold value and the change in the determined probability is larger than the second reference value is the time point at which the user intends to sleep. In the graph 1940 of FIG. 21, an interval 2120 may be a sleep latency of the user which is an interval between the time point at which the user intends to sleep and the time point at which the user actually begins sleeping.

As described above, the processor 120 of the electronic device 101 according to various embodiments may extract values indicating the state of the user from one or more identified signals within the reflection signal of the RF signal. The processor 120 may determine the time point at which the user intends to sleep and the time point at which the user actually begins sleeping by determining the probability of the sleep state of the user on the basis of the extracted values and monitoring the determined probability or the change in the determined probability. The processor 120 may determine the sleep latency of the user on the basis of the determined time points. In other words, the electronic device 101 according to various embodiments may determine the sleep latency corresponding to a parameter indicating whether the user has insomnia without any user input.

Figure 22:
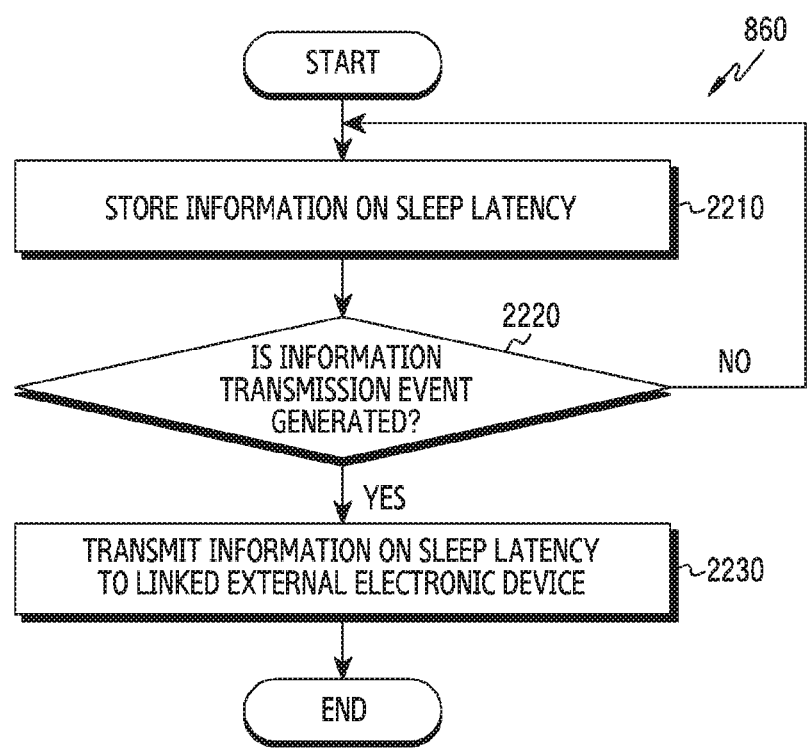
FIG. 22 illustrates an example of the operation of the electronic device for processing information on the sleep latency according to various embodiments.

FIG. 22 illustrates an example of the operation of the electronic device for processing information on the sleep latency according to various embodiments. The operation may be performed by the electronic device 101 illustrated in FIG. 1 or an element (for example, the processor 210) included in the electronic device 101.

In FIG. 22, operations 2210 to 2230 may be related to operation 860 of FIG. 8.

Referring to FIG. 22, in operation 2210, the processor 120 may store information on the sleep latency. The processor 120 may store the information on the sleep latency in order to process the information on the sleep latency through operation 2220 or operation 2230. For example, the processor 120 may store the information on the sleep latency in the memory 130 to transmit the information on the sleep latency to an external electronic device.

In operation 2220, the processor 120 may monitor whether an information transmission event is generated. The information transmission event may be an event for triggering transmission of the information on the sleep latency. According to some embodiments, the information transmission event may indicate that a time point at which the information on the sleep latency is transmitted arrives. For example, the processor 120 may control the communication module 220 to transmit the information on the sleep latency to an external electronic device linked to the electronic device 101 according to a predetermined period (for example, every specific hour, daily, weekly, or monthly). According to other embodiments, the information transmission event may be generation (or establishment) of the connection between an external electronic device and the electronic device 101. For example, the processor 120 may control the communication module 220 to transmit the information on the sleep latency in response to the generation of the connection with the external electronic device linked to the electronic device 101. According to other embodiments, the information transmission event may be operation of the electronic device 101 in a charging state. For example, the electronic device 101 may be a device that requires battery charging. The electronic device 101 may operate in the charging state in order to secure power consumed by transmission of the information on the sleep latency or may control the communication module 220 to transmit the information on the sleep latency in response to the identification of remaining power of the battery of the electronic device 101 larger than or equal to a threshold value.

When the information transmission event is generated, the processor 120 may perform operation 2230. However, when the information transmission event is generated, the processor 120 may repeatedly perform operation 2210 and operation 2220.

In operation 2230, when the information transmission event is generated, the processor 120 may transmit the information on the sleep latency to an external electronic device linked to the electronic device 101. The transmitted information on the sleep latency may be output by the external electronic device. For example, the transmitted information on the sleep latency may be displayed on a display of the external electronic device. In another example, the transmitted information on the sleep latency may be output through vibration, a sound, or an indication. The transmitted information on the sleep latency may be used to control the function of the external electronic device. In this case, the external electronic device may be a medical device for sleep treatment of the user.

As described above, the processor 120 of the electronic device 101 according to various embodiments may improve usability of the information on the sleep latency by sharing the information on the sleep latency with the external electronic device.

Figure 23:
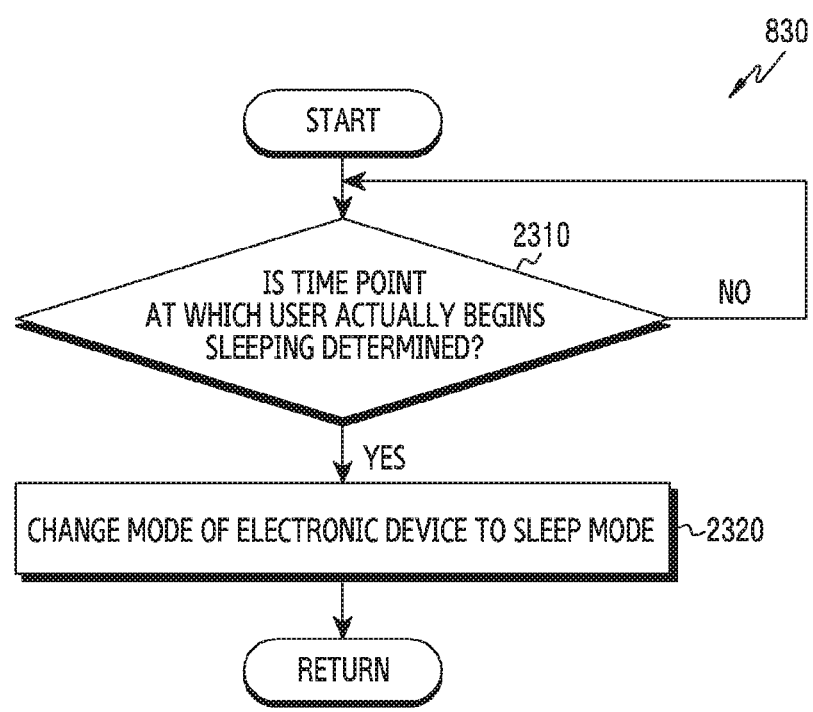
FIG. 23 illustrates an example of the operation of the electronic device for changing a mode according to various embodiments.

FIG. 23 illustrates an example of the operation of the electronic device for changing a mode according to various embodiments. The operation may be performed by the electronic device 101 illustrated in FIG. 1 or an element (for example, the processor 120) included in the electronic device 101.

In FIG. 23, operations 2310 to 2320 may be related to operation 830 of FIG. 8.

Referring to FIG. 23, in operation 2310, the processor 120 may monitor whether to determine a time point at which the user actually begins sleeping. The processor 120 may identify whether the time point at which the user actually begins sleeping is determined in order to determine a time point at which the mode of the electronic device is changed. When the time point at which the user actually begins sleeping is determined, the processor 120 may perform operation 2320. However, when the time point at which the user actually begins sleeping is not determined, the processor 120 may repeatedly perform operation 2310.

In operation 2320, when the time point at which the user actually begins sleeping is determined, the processor 120 may change the mode of the electronic device 101 to a sleep mode. The sleep mode may be a mode for assisting the user in maintaining the sleep state. The sleep mode may be a mode for facilitating the sleep of the user. For example, the processor 120 may control a brightness of a lighting device included in the electronic device 101 in response to the determination of the time point at which the user actually begins sleeping. In another example, the processor 120 may change an intensity of a sound signal (that is, control a volume) output from the speaker 282 included in the electronic device 101 or change a type of the sound signal (that is, change music being reproduced) in response to the determination of the time point at which the user actually begins sleeping. In another example, the processor 120 may change an operation period of the RF sensor 240N or an operation period of the illumination sensor 240K in response to the determination of the time point at which the user actually begins sleeping. In another example, when the electronic device 101 is a device including a display such as a TV, the processor 120 may reduce brightness of a screen output through the display or the number of devices (for example, LEDs or color filters) of the display for outputting or emitting light in response to the determination of the time point at which the user actually begins sleeping.

As described above, the processor 120 of the electronic device 101 according to various embodiments may assist the user in maintaining sleep by controlling the change in the mode of the electronic device 101 in response to the determination of the time point at which the user actually begins sleeping.

The method of the electronic device according to various embodiments as described above may include an operation of acquiring first biometric information and second biometric information through a biometric signal detection sensor of the electronic device, an operation of identifying a first change of the first biometric information and a second change of the second biometric information, an operation of determining a state of an object related to a sleep on the basis of at least a portion of the first change and the second change, and an operation of estimating a sleep latency related to the object.

According to some embodiments, the biometric signal detection sensor may include an RF sensor, and the operation of estimating the sleep latency may include an operation of acquiring motion information of the object through the RF sensor and an operation of estimating the sleep latency on the basis of at least a portion of the first change, the second change, or the motion information According to other embodiments, the electronic device may further include an image sensor, and the operation of estimating the sleep latency may include an operation of acquiring image information of the object through the image sensor, acquire motion information of the object on the basis of at least a portion of the acquired image information and an operation estimating the sleep latency on the basis of at least a portion of the first change, the second change, or the motion information.

According to other embodiments, the first biometric information may include information on breath of the object, and the second biometric information may include information on a heart rate of the object.

The method of the electronic device according to various embodiments may include an operation of receiving first biometric information and second biometric information on an external object measured by an external electronic device through a communication circuit of the electronic device, an operation of identifying a first change of the first biometric information and a second change of the second biometric information, an operation of determining a state of an object related to a sleep on the basis of at least a portion of the first change and the second change, and an operation of estimating a sleep latency related to the object on the basis of at least a portion of the state.

The method of the electronic device according to various embodiments may include an operation of transmitting a Radio Frequency (RF) signal, an operation of receiving a reflection signal of the RF signal; identifying one or more signals indicating a state of a user within the received reflection signal, an operation of monitoring a change (difference) in data determined on the basis of the one or more signals according to a time, an operation of determining that a time point at which the user actually begins sleeping is a time point at which the monitored change is smaller than a first reference value, an operation of determining that a time point at which the user intends to sleep is a second time point at which the monitored change is larger than a second reference value, an operation of determining that a sleep latency of the user is a time interval between the first time point and the second time point, and an operation of storing information on the determined time interval.

According to some embodiments, the operation of identifying the one or more signals may include an operation of monitoring the received reflection signal, execute the stored instructions in order to monitor the received reflection signal, an operation of identifying the one or more signals within the received reflection signal in response to monitoring that a change in the reflection signal is output of a predetermined range, and an operation of storing the data in the memory or temporarily store the data in response to monitoring that the change in the reflection signal is output of the predetermined range. For example, the predetermined range may be configured to identify whether the user is located in a specified area. In another example, the operation of determining the time point at which the user intends to sleep may include an operation of identifying the stored data in response to the determination that the time point at which the user actually begins sleeping is the first time point, an operation of identifying the second time point at which the change within the stored data is larger than the second reference value, and an operation of determining that the time point at which the user intends to sleep is the second time point.

According to other embodiments, the one or more signals may include a first signal indicating motion of the user, a second signal indicating a breath state of the user, or a third signal indicating a heartbeat state of the user. For example, the method of the electronic device may further include an operation of acquiring a first value indicating the motion of the user from the first signal, acquiring a second value indicating the breath state of the user from the second signal, acquiring a third value indicating the heartbeat state of the user from the third signal, and determining that a probability of a sleep state of the user is the data on the basis of at least a portion of the first value, the second value, and the third value In another example, the electronic device may include a plurality of filters and an RF sensor configured to receive the reflect signal, and the operation of identifying the one or more signals may include an operation of identifying the first signal related to a first band within the received reflection signal through a first filter in the plurality of filters, identifying the second signal related to a second band within the received reflection signal through a second filter in the plurality of filters, and identifying the third signal related to a third band within the received reflection signal through a third filter in the plurality of filters.

According to other embodiments, the method of the electronic device may further include an operation of measuring illumination of light around the electronic device and an operation of receiving a sound signal around the electronic device, and the operation of determining the time point at which the user actually begins sleeping may include an operation of determining the time point at which the user actually begins sleeping on the basis of at least a portion of information on the illumination and information on the sound signal and the operation of determining the time point at which the user intends to sleep may include an operation of determining the time point at which the user intends to sleep on the basis of at least a portion of the information on the illumination and the information on the sound signal.

According to other embodiments, the method of the electronic device may further include an operation of controlling a brightness of an environment in which the electronic device is located in response to the determination of the time point at which the user actually begins sleeping.

According to other embodiments, the method of the electronic device may further include an operation of transmitting information on the determined time interval to the external electronic device.

According to other embodiments, the method of the electronic device may further include an operation of changing the output sound signal in response to the determination of the time point at which the user actually begins sleeping.

According to other embodiments, the operation of transmitting the RF signal may include an operation of transmitting the RF signal through the plurality of beams.

Methods according to embodiments stated in claims and/or specifications of the disclosure may be implemented in hardware, software, or a combination of hardware and software.

When the methods are implemented by software, a computer-readable storage medium for storing one or more programs (software modules) may be provided. The one or more programs stored in the computer-readable storage medium may be configured for execution by one or more processors within the electronic device. The at least one program may include instructions that cause the electronic device to perform the methods according to various embodiments of the disclosure as defined by the appended claims and/or disclosed herein.

The programs (software modules or software) may be stored in non-volatile memories including a random access memory and a flash memory, a Read Only Memory (ROM), an Electrically Erasable Programmable Read Only Memory (EEPROM), a magnetic disc storage device, a Compact Disc-ROM (CD-ROM), Digital Versatile Discs (DVDs), or other type optical storage devices, or a magnetic cassette. Alternatively, any combination of some or all of the may form a memory in which the program is stored. Further, a plurality of such memories may be included in the electronic device.

In addition, the programs may be stored in an attachable storage device which may access the electronic device through communication networks such as the Internet, Intranet, Local Area Network (LAN), Wide LAN (WLAN), and Storage Area Network (SAN) or a combination thereof. Such a storage device may access the electronic device via an external port. Further, a separate storage device on the communication network may access a portable electronic device.

In the above-described detailed embodiments of the disclosure, a component included in the disclosure is expressed in the singular or the plural according to a presented detailed embodiment. However, the singular form or plural form is selected for convenience of description suitable for the presented situation, and various embodiments of the disclosure are not limited to a single element or multiple elements thereof. Further, either multiple elements expressed in the description may be configured into a single element or a single element in the description may be configured into multiple elements.

While the disclosure has been shown and described with reference to certain embodiments thereof, it will be understood by those skilled in the art that various changes in form and details may be made therein without departing from the scope of the disclosure. Therefore, the scope of the disclosure should not be defined as being limited to the embodiments, but should be defined by the appended claims and equivalents thereof.

The invention claimed is:

1. An electronic device comprising:
a memory configured to store instructions;
an RF sensor configured to transmit a Radio Frequency (RF) signal and receive a reflection signal of the RF signal; and
at least one processor coupled to the RF sensor and the memory and configured to execute the stored instructions in order to:
identify one or more signals indicating a state of a user within the received reflection signal,
monitor a change in data determined based on the one or more signals according to a time,
determine that a time point at which the user actually begins sleeping is a first time point at which the monitored change is smaller than a first reference value,
determine that a time point at which the user intends to sleep is a second time point at which the monitored change is larger than a second reference value,
determine that a sleep latency of the user is a time interval between the first time point and the second time point, and
store information on the determined time interval.

2. The electronic device of claim 1, wherein at least one processor is configured to execute the stored instructions in order to:
monitor the received reflection signal,
identify the one or more signals within the received reflection signal in response to monitoring that a change in the reflection signal is output of a predetermined range, and
store the data in the memory or temporarily store the data in response to monitoring that the change in the reflection signal is output of the predetermined range.

3. The electronic device of claim 2, wherein the predetermined range is configured to identify whether the user is located in a specified area.

4. The electronic device of claim 2, wherein at least one processor is configured to execute the stored instructions in order to:
identify the stored data in response to the determination that the time point at which the user actually begins sleeping is the first time point,
identify the second time point at which the change within the stored data is larger than the second reference value, and
determine that the time point at which the user intends to sleep is the second time point.

5. The electronic device of claim 1, wherein the one or more signals comprise a first signal indicating motion of the user, a second signal indicating a breath state of the user, or a third signal indicating a heartbeat state of the user.

6. The electronic device of claim 5, wherein at least one processor is configured to execute the stored instructions in order to:
acquire a first value indicating the motion of the user from the first signal,
acquire a second value indicating the breath state of the user from the second signal,
acquire a third value indicating the heartbeat state of the user from the third signal, and
determine that a probability of a sleep state of the user is the data, based on at least a portion of the first value, the second value, and the third value.

7. The electronic device of claim 5, wherein the RF sensor comprises a plurality of filters, and at least one processor is configured to execute the stored instructions in order to:

identify the first signal related to a first band within the received reflection signal through a first filter in the plurality of filters, identify the second signal related to a second band within the received reflection signal through a second filter in the plurality of filters, and identify the third signal related to a third band within the received reflection signal through a third filter in the plurality of filters.

8. The electronic device of claim 1, further comprising an illumination sensor configured to measure illumination of light around the electronic device and a microphone configured to receive a sound signal around the electronic device, wherein at least one processor is further configured to execute the stored instructions in order to:

determine a time point at which the user actually begins sleeping based on at least a portion of information on the illumination and information on the sound signal, and determine a time point at which the user intends to sleep based on at least a portion of the information on the illumination and the information on the sound signal.

9. The electronic device of claim 1, further comprising a circuit configured to control a brightness of an environment in which the electronic device is located, wherein at least one processor is further configured to execute the stored instructions in order to control the brightness of the environment in which the electronic device is located in response to the determination of the time point at which the user actually begins sleeping.

10. The electronic device of claim 1, further comprising a communication interface configured to communicate with an external electronic device, wherein at least one processor is configured to execute the stored instructions in order to transmit information on the determined time interval to the external electronic device.

11. The electronic device of claim 1, further comprising a speaker configured to output a sound signal, wherein at least one processor is configured to execute the stored instructions in order to change the output sound signal in response to the determination of the time point at which the user actually begins sleeping.

12. The electronic device of claim 1, wherein the RF sensor comprises a transmission circuit configured to transmit the RF signal through a plurality of beams and a plurality of antennas, and at least one processor is configured to execute the stored instructions in order to transmit the RF signal through the plurality of beams.

13. A method of an electronic device, the method comprising:

transmitting a Radio Frequency (RF) signal;

receiving a reflection signal of the RF signal;

identifying one or more signals indicating a state of a user within the received reflection signal;

monitoring a change in data determined based on the one or more signals according to a time;

determining that a time point at which the user actually begins sleeping is a time point at which the monitored change is smaller than a first reference value;

determining that a time point at which the user intends to sleep is a second time point at which the monitored change is larger than a second reference value;

determining that a sleep latency of the user is a time interval between the first time point and the second time point; and storing information on the determined time interval.

14. The method of claim 13, further comprising:

monitoring the received reflection signal;

identifying the one or more signals within the received reflection signal in response to monitoring that a change in the reflection signal is output of a predetermined range; and storing the data in the memory or temporarily store the data in response to monitoring that the change in the reflection signal is output of the predetermined range.

15. The method of claim 13, further comprising:

determining a time point at which the user actually begins sleeping based on at least a portion of information on illumination of light and information on the sound signal; and determining a time point at which the user intends to sleep based on at least a portion of the information on illumination of light and information on the sound signal.

16. The method of claim 13, further comprising:

controlling a brightness of an environment in which the electronic device is located in response to the determination of the time point at which the user actually begins sleeping.

17. The method of claim 13, further comprising:

transmitting information on the determined time interval to the external electronic device.

18. The method of claim 13, further comprising:

changing an output sound signal in response to the determination of the time point at which the user actually begins sleeping.

19. The method of claim 13, further comprising:

transmitting the RF signal through a plurality of beams and a plurality of antennas.

* * * * *